(12) United States Patent
Fluhr et al.

(10) Patent No.: US 10,238,113 B2
(45) Date of Patent: Mar. 26, 2019

(54) METHOD FOR PROTECTING PLANTS FROM STRESS AND SENESCENCE

(71) Applicants: BEN-GURION UNIVERSITY OF THE NEGEV RESEARCH AND DEVELOPMENT AUTHORITY, Beer Sheva (IL); YEDA RESEARCH AND DEVELOPMENT CO. LTD., Rehovot (IL)

(72) Inventors: Robert Fluhr, Rehovot (IL); Moshe Sagi, Lehavim (IL)

(73) Assignees: Yeda Research and Development Co. Ltd. at The Weizmann Institute of Science, Rehovot (IL); Ben-Gurion University of The Negev research and Development Authority, Beer Sheva (IL)

( * ) Notice: Subject to any disclaimer, the term of this patent is extended or adjusted under 35 U.S.C. 154(b) by 81 days.

(21) Appl. No.: 14/656,693

(22) Filed: Mar. 12, 2015

(65) Prior Publication Data
US 2015/0181884 A1 Jul. 2, 2015

Related U.S. Application Data

(62) Division of application No. 12/863,986, filed as application No. PCT/IL2009/000120 on Feb. 1, 2009, now abandoned.

(60) Provisional application No. 61/024,930, filed on Jan. 31, 2008.

(51) Int. Cl.
*A01N 3/00* (2006.01)
*A01N 43/50* (2006.01)
*A01N 43/90* (2006.01)
*A01N 47/28* (2006.01)
*C12N 15/82* (2006.01)

(52) U.S. Cl.
CPC .............. *A01N 47/28* (2013.01); *A01N 3/00* (2013.01); *A01N 43/50* (2013.01); *A01N 43/90* (2013.01); *C12N 15/8243* (2013.01); *C12N 15/8269* (2013.01); *C12N 15/8271* (2013.01)

(58) Field of Classification Search
CPC ...................................................... A01N 47/28
See application file for complete search history.

(56) References Cited

U.S. PATENT DOCUMENTS 2,382,326 A * 8/1945 Mecca .................. A01N 47/36
33/20.4
2010/0011456 A1 1/2010 Mathur

FOREIGN PATENT DOCUMENTS

WO 02/16655 2/2002
WO 2004/061080 7/2004

OTHER PUBLICATIONS

Roch-Ramel (W. N. Kelley et al. (eds.), Chapter 9Uric Acid Springer-Verlag Berlin Heidelberg, 1978).*
Beranrdi (Science of the Total Environment 407( 2009) 2383-2389).*
Alamillo et al (The Plant Journal (2001) 25(5), 529-540).*
KEGG Compound: C00366 (2016).*
KEGG Compound: C00499 (2016).*
Purcell et al (Crop Sci. 40:1062-1070 (2000).*
Serraj et al (Plant Physiology, Jan. 1999, vol. 119, pp. 289-296).*
Li-Geng et al (Photosynthetica 29(4): 529-533, 1993).*
Kessler et al (Plant Physiol. Nov. 1959; 34(6): 605-608).*
Xingyuan (Journal of Anhui Agricultural University, 1995).*
Xu et al (Journal of Guangxi Agricultural University, 1997).*
Xu et al (Journal of Guangxi Agricultural University, 1997) (Year: 1997).*
Li-Geng et al (Photosynthetica 29(4): 529-533, 1993) (Year: 1993).*
Alamillo and Garcia-Olmedo (2001) Effects of urate, a natural inhibitor of peroxynitrite-mediated toxicity, in the response of *Arabidopsis thaliana* to the bacterial pathogen Pseudomonas syringae. Plant Journal 25(5): 529-540.
Alsheikh et al., (2005) Phosphorylation regulated ion-binding is a property shared by the acidic subclass dehydrins. Plant Cell Environ 28(9): 1114-1122.
Brychkova et al., (2007) Sulfite oxidase protects plants against sulfur dioxide toxicity. Plant J 50(4): 696-709.
Brychkova et al., (2008) A critical role for ureides in dark and senescenceinduced purine remobilization is unmasked in the Atxdh1 *Arabidopsis* mutant. Plant Journal 54(3): 496-509.
Buchanan-Wollaston et al., (2005) Comparative transcriptome analysis reveals significant differences in gene expression and signalling pathways between developmental and dark/starvation-induced senescence in *Arabidopsis*. Plant J 42(4): 567-585.
Callard et al., (1996) Novel Molecular Markers for Late Phases of the Growth Cycle of *Arabidopsis thaliana* Cell-Suspension Cultures are Expressed during Organ Senescence. Plant Physiol 112(2): 705-715.
Corpas et al., (1997) A role for leaf peroxisomes in the catabolism of purines. J Plant Physiol 151: 246-250.
Fryer et al., (2002) Imaging of photo-oxidative stress responses in leaves. J Exp Bot 53(372): 1249-1254.
Gepstein et al., (2003) Large-scale identification of leaf senescence-associated genes. Plant J 36(5): 629-642.

(Continued)

*Primary Examiner* — Lee A Visone
(74) *Attorney, Agent, or Firm* — Rodney J. Fuller; Booth Udall Fuller, PLC

(57) ABSTRACT

The present invention relates to regulation of ureide levels for optimal plant survival during nutrient remobilization such as occurs during normal growth, dark stress and senescence. Plants can be genetically engineered or selected using a suitable gene marker to have enhanced ureide accumulation. The present invention further provides methods of protecting plants, or extending the shelf life of fresh plant produce by application of exogenous ureides.

12 Claims, 13 Drawing Sheets
Specification includes a Sequence Listing.

(56) References Cited

OTHER PUBLICATIONS

Gepstein (2004) Leaf senescence—not just a 'wear and tear' phenomenon. Genome Biology 5: 212 (3 pages).
Guo and Crawford (2005) Arabidopsis Nitric Oxide Synthase1 is Targeted to Mitochondria and Protects against Oxidative Damage and Dark-Induced Senescence. Plant Cell 17(12): 3436-3450.
Harrison (2002) Structure and function of xanthine oxidoreductase: where are we now? Free Radic Biol Med 33(4): 774-797.
Hesberg et al., (2004) Tandem orientation of duplicated Xanthine Dehydrogenase genes from Arabidopsis thaliana: differential gene expression and enzyme activities. J Biol Chem 279(14): 13547-13554.
Jabs et al., (1996) Initiation of runaway cell death in an Arabidopsis mutant by extracellular superoxide. Science 273 (5283): 1853-1856.
Koch and Slusarenko (1990) Arabidopsis is Susceptible to Infection by a Downy Mildew Fungus. Plant Cell 2(5): 437-445.
Lehner et al., (2004) Technique review: how to use RNA interference. Brief Functional Genomics 3(1): 68-83.
Miao et al., (2004) Targets of the WRKY53 transcription factor and its role during leaf senescence in Arabidopsis. Plant Mol Biol 55(6): 853-867.
Mohanty et al., (1997) A highly sensitive fluorescent micro-assay of H2O2 release from activated human leukocytes using a dihydroxyphenoxazine derivative. J Immunol Methods 202(2): 133-141.
Munoz et al., (2011) An alternative pathway for ureide usage in legumes: enzymatic formation of a ureidoglycolate adduct in Cicer arietinum and Phaseolus vulgaris. J Exp Bot 62(1): 307-318.
Nakagawa et al., (2007) The RNAi-mediated silencing of xanthine dehydrogenase impairs growth and fertility and accelerates leaf senescence in transgenic Arabidopsis plants. Plant Cell Physiol 48(10): 1484-1495.
Nguyen (1986) Plant xanthine dehydrogenase: its distribution, properties and function. Physiologie Végétale 24: 263-281.
Park et al., (2007) The Senescence-Induced Staygreen Protein Regulates Chlorophyll Degradation. Plant Cell 19(5): 1649-1664.
Pastori and Del Rio (1997) Natural Senescence of Pea Leaves (An Activated Oxygen-Mediated Function for Peroxisomes). Plant Physiol 113(2): 411-418.
Pruzinska et al., (2005) Chlorophyll breakdown in senescent Arabidopsis leaves. Characterization of chlorophyll catabolites and of chlorophyll catabolic enzymes involved in the degreening reaction. Plant Physiol 139(1): 52-63.
Rentel et al., (2004) OXI1 kinase is necessary for oxidative burst-mediated signalling in Arabidopsis. Nature 427 (6977): 858-861.
Reumann et al., (2007) Proteome analysis of Arabidopsis leaf peroxisomes reveals novel targeting peptides, metabolic pathways, and defense mechanisms. Plant Cell 19(10): 3170-93.
Sagi et al., (1998) The Mo-hydroxylases xanthine dehydrogenase and aldehyde oxidase in ryegrass as affected by nitrogen and salinity. Plant Science 135(2): 125-135.
Sagi et al., (1999) Aldehyde Oxidase and Xanthine Dehydrogenase in a flacca Tomato Mutant with Deficient Abscisic Acid and Wilty Phenotype. Plant Physiol 120(2): 571-578.
Sagi et al., (2002) The absence of molybdenum cofactor sulfuration is the primary cause of the flacca phenotype in tomato plants. Plant J 31(3): 305-317.
Sagi et al., (2004) Plant respiratory burst oxidase homologs impinge on wound responsiveness and development in Lycopersicon esculentum. Plant Cell 16(3): 616-628.
Sagi and Fluhr (2001) Superoxide production by plant homologues of the gp91(phox) NADPH oxidase. Modulation of activity by calcium and by tobacco mosaic virus infection. Plant Physiol 126(3): 1281-1290.
Tanaka et al., (2003) The Arabidopsis-accelerated cell death gene ACD1 is involved in oxygenation of pheophorbide a: inhibition of the pheophorbide a oxygenase activity does not lead to the "stay-green" phenotype in Arabidopsis. Plant Cell Physiol 44(12): 1266-1274.
Todd et al., (2006) Update on ureide degradation in legumes. J Exp Bot 57(1): 5-12.
Vogels and Van Der Drift (1970) Differential analyses of glyoxylate derivatives. Anal Biochem 33(1): 143-157.
Wang et al., (2010) Caenorhabditis elegans transthyretin-like protein TTR-52 mediates recognition of apoptotic cells by the CED-1 phagocyte receptor. Nat Cell Biol 12(7): 655-664.
Weaver et al., (1998) A comparison of the expression patterns of several senescence-associated genes in response to stress and hormone treatment. Plant Mol Biol 37(3): 455-469.
Werner (2010) Ureide catabolism in Arabidopsis thaliana and Escherichia coli. Nat Chem Biol 6(1): 19-21.
Yesbergenova et al., (2005) The plant Mo-hydroxylases aldehyde oxidase and xanthine dehydrogenase have distinct reactive oxygen species signatures and are induced by drought and abscisic acid. Plant J 42(6): 862-876.
Zdunek-Zastocka Lips (2003) Plant molybdoenzymes and their response to stress. ACTA Physiologiae Plantarum 25 (4): 437-452.
Zrenner et al., (2006) Pyrimidine and purine biosynthesis and degradation in plants. Annu Rev Plant Biol 57: 805-836.
Database EPO Proteins Rice stress-related protein #32 Oct. 7, 2004 XP002525116 retrieved from EBI database accession No. ADQ15655.
Enzyme Report for ureidoglycolate lyase downloaded from BRENDA on Dec. 9, 2014 (http://www.brenda-enzymes.org/enzyme.php?ecno=4.3.2.3#print).

* cited by examiner

SEQUENCE LISTING

```
<160> NUMBER OF SEQ ID NOS: 36

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
gattgttccc gttgcaaggt tgttt                                          25

<210> SEQ ID NO 2
<211> LENGTH: 28
<212> TYPE: DNA
<213> ORGANISM: Artificial Sequence
<220> FEATURE:
<223> OTHER INFORMATION: Synthetics primer

<400> SEQUENCE: 2
tgcaactgag agttgtttat ggattgag                                       28

<210> SEQ ID NO 3
<211> LENGTH: 25
<212> TYPE: DNA
<213> ORGANISM: Artificial Sequence
<220> FEATURE:
<223> OTHER INFORMATION: Synthetics primer

<400> SEQUENCE: 3
aagagtgggg atttttccag cttgt                                          25

<210> SEQ ID NO 4
<211> LENGTH: 27
<212> TYPE: DNA
<213> ORGANISM: Artificial Sequence
<220> FEATURE:
<223> OTHER INFORMATION: Synthetics primer

<400> SEQUENCE: 4
tgcccaatct agtttctgat cttctga                                        27

<210> SEQ ID NO 5
<211> LENGTH: 27
```

<212> TYPE: DNA
<213> ORGANISM: Artificial Sequence
<220> FEATURE:
<223> OTHER INFORMATION: Synthetics primer

<400> SEQUENCE: 5
tttgttaaga ctctcaccgg aaagaca                                          27

<210> SEQ ID NO 6
<211> LENGTH: 27
<212> TYPE: DNA
<213> ORGANISM: Artificial Sequence
<220> FEATURE:
<223> OTHER INFORMATION: Synthetics primer

<400> SEQUENCE: 6
gagggtggat tccttctgga tattgta                                          27

<210> SEQ ID NO 7
<211> LENGTH: 27
<212> TYPE: DNA
<213> ORGANISM: Artificial Sequence
<220> FEATURE:
<223> OTHER INFORMATION: Synthetics primer

<400> SEQUENCE: 7
cactgtttat gtgaaagcca aggaatg                                          27

<210> SEQ ID NO 8
<211> LENGTH: 27
<212> TYPE: DNA
<213> ORGANISM: Artificial Sequence
<220> FEATURE:
<223> OTHER INFORMATION: Synthetics primer

<400> SEQUENCE: 8
cccaagctta aaaccatgta aatgtgg                                          27

<210> SEQ ID NO 9
<211> LENGTH: 27
<212> TYPE: DNA
<213> ORGANISM: Artificial Sequence
<220> FEATURE:
<223> OTHER INFORMATION: Synthetics primer

<400> SEQUENCE: 9
ccatgcgtta aaggaaaggt atgaaaa                                          27

<210> SEQ ID NO 10
<211> LENGTH: 27
<212> TYPE: DNA
<213> ORGANISM: Artificial Sequence
<220> FEATURE:
<223> OTHER INFORMATION: Synthetics primer

<400> SEQUENCE: 10
tgattctcag acgatcttga ggttttg                                          27

<210> SEQ ID NO 11
<211> LENGTH: 30
<212> TYPE: DNA
<213> ORGANISM: Artificial Sequence
<220> FEATURE:
<223> OTHER INFORMATION: Synthetics primer

<400> SEQUENCE: 11

```
tcaaagaaaa gaaagatgtt accaaagtgg                               30

<210> SEQ ID NO 12
<211> LENGTH: 27
<212> TYPE: DNA
<213> ORGANISM: Artificial Sequence
<220> FEATURE:
<223> OTHER INFORMATION: Synthetics primer

<400> SEQUENCE: 12
gtgcatctgt aataactcct tgggaat                                  27

<210> SEQ ID NO 13
<211> LENGTH: 28
<212> TYPE: DNA
<213> ORGANISM: Artificial Sequence
<220> FEATURE:
<223> OTHER INFORMATION: Synthetics primer

<400> SEQUENCE: 13
tgatgttgga caaatagaag gagcgttt                                 28

<210> SEQ ID NO 14
<211> LENGTH: 29
<212> TYPE: DNA
<213> ORGANISM: Artificial Sequence
<220> FEATURE:
<223> OTHER INFORMATION: Synthetics primer

<400> SEQUENCE: 14
tattcggatt ccccttgaga agcgaaaca                                29

<210> SEQ ID NO 15
<211> LENGTH: 28
<212> TYPE: DNA
<213> ORGANISM: Artificial Sequence
<220> FEATURE:
<223> OTHER INFORMATION: Synthetics primer

<400> SEQUENCE: 15
tgatattgga caaatagaag gagcgttt                                 28

<210> SEQ ID NO 16
<211> LENGTH: 29
<212> TYPE: DNA
<213> ORGANISM: Artificial Sequence
<220> FEATURE:
<223> OTHER INFORMATION: Synthetics primer

<400> SEQUENCE: 16
tgcatttgga ttacccttga gaagagaaa                                29

<210> SEQ ID NO 17
<211> LENGTH: 26
<212> TYPE: DNA
<213> ORGANISM: Artificial Sequence
<220> FEATURE:
<223> OTHER INFORMATION: Synthetics primer

<400> SEQUENCE: 17
agactcacca acagcttgac caattt                                   26

<210> SEQ ID NO 18
<211> LENGTH: 26
<212> TYPE: DNA
<213> ORGANISM: Artificial Sequence
```

```
<220> FEATURE:
<223> OTHER INFORMATION: Synthetics primer

<400> SEQUENCE: 18
cacctagtcc atcatccgag ctagag                                          26

<210> SEQ ID NO 19
<211> LENGTH: 25
<212> TYPE: DNA
<213> ORGANISM: Artificial Sequence
<220> FEATURE:
<223> OTHER INFORMATION: Synthetics primer

<400> SEQUENCE: 19
gattgttccc gttgcaaggt tgttt                                           25

<210> SEQ ID NO 20
<211> LENGTH: 28
<212> TYPE: DNA
<213> ORGANISM: Artificial Sequence
<220> FEATURE:
<223> OTHER INFORMATION: Synthetics primer

<400> SEQUENCE: 20
tgcaactgag agttgtttat ggattgag                                        28

<210> SEQ ID NO 21
<211> LENGTH: 25
<212> TYPE: DNA
<213> ORGANISM: Artificial Sequence
<220> FEATURE:
<223> OTHER INFORMATION: Synthetics primer

<400> SEQUENCE: 21
aagagtgggg atttttccag cttgt                                           25

<210> SEQ ID NO 22
<211> LENGTH: 27
<212> TYPE: DNA
<213> ORGANISM: Artificial Sequence
<220> FEATURE:
<223> OTHER INFORMATION: Synthetics primer

<400> SEQUENCE: 22
tgcccaatct agtttctgat cttctga                                         27

<210> SEQ ID NO 23
<211> LENGTH: 27
<212> TYPE: DNA
<213> ORGANISM: Artificial Sequence
<220> FEATURE:
<223> OTHER INFORMATION: Synthetics primer

<400> SEQUENCE: 23
tttgttaaga ctctcaccgg aaagaca                                         27

<210> SEQ ID NO 24
<211> LENGTH: 27
<212> TYPE: DNA
<213> ORGANISM: Artificial Sequence
<220> FEATURE:
<223> OTHER INFORMATION: Synthetics primer

<400> SEQUENCE: 24
gagggtggat tccttctgga tattgta                                         27
```

```
<210> SEQ ID NO 25
<211> LENGTH: 27
<212> TYPE: DNA
<213> ORGANISM: Artificial Sequence
<220> FEATURE:
<223> OTHER INFORMATION: Synthetics primer

<400> SEQUENCE: 25
cactgtttat gtgaaagcca aggaatg                                              27

<210> SEQ ID NO 26
<211> LENGTH: 27
<212> TYPE: DNA
<213> ORGANISM: Artificial Sequence
<220> FEATURE:
<223> OTHER INFORMATION: Synthetics primer

<400> SEQUENCE: 26
cccaagctta aaaccatgta aatgtgg                                              27

<210> SEQ ID NO 27
<211> LENGTH: 27
<212> TYPE: DNA
<213> ORGANISM: Artificial Sequence
<220> FEATURE:
<223> OTHER INFORMATION: Synthetics primer

<400> SEQUENCE: 27
ccatgcgtta aaggaaaggt atgaaaa                                              27

<210> SEQ ID NO 28
<211> LENGTH: 27
<212> TYPE: DNA
<213> ORGANISM: Artificial Sequence
<220> FEATURE:
<223> OTHER INFORMATION: Synthetics primer

<400> SEQUENCE: 28
tgattctcag acgatcttga ggttttg                                              27

<210> SEQ ID NO 29
<211> LENGTH: 30
<212> TYPE: DNA
<213> ORGANISM: Artificial Sequence
<220> FEATURE:
<223> OTHER INFORMATION: Synthetics primer

<400> SEQUENCE: 29
tcaaagaaaa gaaagatgtt accaaagtgg                                           30

<210> SEQ ID NO 30
<211> LENGTH: 27
<212> TYPE: DNA
<213> ORGANISM: Artificial Sequence
<220> FEATURE:
<223> OTHER INFORMATION: Synthetics primer

<400> SEQUENCE: 30
gtgcatctgt aataactcct tgggaat                                              27

<210> SEQ ID NO 31
<211> LENGTH: 28
<212> TYPE: DNA
<213> ORGANISM: Artificial Sequence
<220> FEATURE:
<223> OTHER INFORMATION: Synthetics primer
```

```
<400> SEQUENCE: 31
tgatgttgga caaatagaag gagcgttt                                        28

<210> SEQ ID NO 32
<211> LENGTH: 29
<212> TYPE: DNA
<213> ORGANISM: Artificial Sequence
<220> FEATURE:
<223> OTHER INFORMATION: Synthetics primer

<400> SEQUENCE: 32
tattcggatt ccccttgaga agcgaaaca                                       29

<210> SEQ ID NO 33
<211> LENGTH: 28
<212> TYPE: DNA
<213> ORGANISM: Artificial Sequence
<220> FEATURE:
<223> OTHER INFORMATION: Synthetics primer

<400> SEQUENCE: 33
tgatattgga caaatagaag gagcgttt                                        28

<210> SEQ ID NO 34
<211> LENGTH: 29
<212> TYPE: DNA
<213> ORGANISM: Artificial Sequence
<220> FEATURE:
<223> OTHER INFORMATION: Synthetics primer

<400> SEQUENCE: 34
tgcatttgga ttacccttga gaagagaaa                                       29

<210> SEQ ID NO 35
<211> LENGTH: 26
<212> TYPE: DNA
<213> ORGANISM: Artificial Sequence
<220> FEATURE:
<223> OTHER INFORMATION: Synthetics primer

<400> SEQUENCE: 35
agactcacca acagcttgac caattt                                          26

<210> SEQ ID NO 36
<211> LENGTH: 26
<212> TYPE: DNA
<213> ORGANISM: Artificial Sequence
<220> FEATURE:
<223> OTHER INFORMATION: Synthetics primer

<400> SEQUENCE: 36
cacctagtcc atcatccgag ctagag                                          26
```

METHOD FOR PROTECTING PLANTS FROM STRESS AND SENESCENCE

CROSS-REFERENCE TO RELATED APPLICATIONS

This application is a divisional of U.S. patent application Ser. No. 12/863,986, filed Jul. 21, 2010 (published as U.S. Publication No. 20100333273), which is the U.S. National Stage of International Application No. PCT/IL2009/000120, filed Feb. 1, 2009, which claims the benefit of U.S. Provisional Application No. 61/024,930, filed Jan. 31, 2008, the contents of each of which are herein incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 7,178 byte ASCII (text) file named "Seq_List" created on Mar. 11, 2015.

FIELD OF THE INVENTION

The present invention relates to the field of plant survival and adaptation to environmental stress as well as to the preservation of fresh plant produce. Particularly, the present invention relates to the role of ureides in protecting plants and/or plant produce from senescence or stress related damages.

BACKGROUND OF THE INVENTION

The remobilization of plant resources during stress facilitates environmental adaptation. The definitive example of such metabolite reallocation in a leaf is delineated by leaf senescence. In addition to natural ageing, many environmental factors such as temperature, drought, nutrient supply, pathogen attack and light conditions can hasten senescence. For example, dark-induced stress is characterized by leaf yellowing, due to the breakdown of chlorophyll and general chloroplast degradation. Metabolic changes during senescence are associated with the transition from nutrient assimilation to metabolite turnover that is accelerated by catabolic activities. For example, in legumes, the catabolic products of purine, the ureides, can provide the plant with readily transportable metabolites that excel in a high nitrogen to carbon ratio. It has been suggested that the carbon nitrogen ratio generated in energy-conserving purine catabolism may be critical for the plants survival under stress conditions.

Little is known about the control of purine catabolism in leaves. Purine catabolism starts with the conversion of adenosine monophosphate (AMP) to inosine monophosphate (IMP) by AMP deaminase (AMPD, E.C.3.5.4.6) that leads by multiple pathways to the production of oxypurines such as xanthine and hypoxanthine. However, further degradation of xanthine to urate requires the activity of the pivotal enzyme, xanthine dehydrogenase (XDH, EC 1.1.1.204). Urate is further metabolized to the ureide, allantoin, through urate oxidase (UO) and transthyretin-like protein (TLP). In *Arabidopsis*, allantoinase (ALN, E.C. 3.5.2.5.) converts allantoin to allantoate, followed by allantoate amidinohydrolase (AAH, E.C. 3.5.3.9.), that converts allantoate to ureidoglycolate and ammonia. A putative ureidoglycolate lyase converts ureidoglycolate to the basic metabolic building blocks, glyoxylate and urea.

XDH contains molybdenum cofactor (MoCo), FAD and NADPH binding domains. The second oxygen in the mono-oxo-MoCo is replaced by a sulfur ligand. When using xanthine/hypoxanthine or NADH as substrates the sulfo-MoCo form of XDH can generate superoxide radicals. In contrast, the desulfo-MoCo form of XDH shows only FAD dependent activity and generats superoxide radical only in the presence of NADH.

Among the two XDH encoding genes detected in the *Arabidopsis* genome (AtXDH1 and AtXDH2), only AtXDH1 responds to environmental stimuli. A specific function of XDH in ageing is not clear, although in both mammalian heart and in plants the activity of XDH is enhanced with age.

Nowhere in the background art is it taught or suggested that ureide metabolism can be regulated to increase plant resistance to stress. Exogenous application of ureides or enhanced endogenous accumulation of ureides for plant protection and, for example, extension of shelf life of produce has not been previously known or suggested in the art.

SUMMARY OF THE INVENTION

The present invention provides compositions and methods for protecting plants or plant produce from stress and senescence. The present invention further provides compositions and methods for extending the shelf life of plant fresh produce including vegetables, fruit, cut branches and flowers. In particular, the present invention provides compositions and methods for protecting harvested agricultural produce from premature senescence and senescence.

It is now disclosed that elevated levels of ureides protect plants from the deleterious effects of senescence and stress. Without wishing to be bound by any theory or mechanism of action, the protection is likely to result from alleviating oxidative stress by scavenging reactive oxygen species. The present invention also identifies the enzymes and enzyme variants that regulate the production of ureides in plants.

The present invention is based in part on the use of experimental models of plant senescence and stress such as extended dark treatment in order to induce metabolite remobilization processes. It is now disclosed for the first time that both dark-induced stress and increased age induced accumulation of the ureides, including allantoin and allantoate, in wild-type leaves. In contrast, under these conditions, in xanthine dehydrogenase-1 (XDH1) compromised plants, xanthine but no ureides accumulated, and accelerated senescence and mortality rates were observed. Thus, a protective role for xanthine dehydrogenase and ureides in senescence was demonstrated.

Unexpectedly, this protection can also be achieved by the exogenous application of ureides to plants or to parts thereof. In particular, the present invention provides compositions and methods comprising exogenous ureides for post-harvest protection of plant fresh produce from senescence and premature senescence.

According to the principles of the invention it is possible to utilize any method that increases cellular ureides at critical times and levels to produce more hardy plants. Plants suffer damage from oxidative stress during drought, cold and other environmental abuse. Without wishing to be bound by any theory or mechanism of action it is envisaged that enhancing the scavenger pathways, specifically through the presence of higher levels of urieds, yields plants that are protected from damage such as damage caused by environmental stress.

According to a first aspect, the present invention provides a method for protecting plants or plant parts from a stress related process, comprising applying to the plant or plant part a composition comprising an amount of at least one ureide effective in decreasing or delaying the stress related process. According to certain embodiments stress related processes include, among others, chlorophyll degradation, oxidative stress, senescence, premature senescence or any combination thereof.

According to certain embodiments the composition comprises 0.001-10 mM ureide, typically 0.01-10 mM ureide, more typically 0.1 mM-0.5 mM ureide. The composition may comprise 0.1 mM ureide or 0.5 mM ureide or any amount in the above specified ranges.

According to some embodiments the plant parts are selected from fruit, vegetables, cut branches and flowers. Other harvested plant parts may be also be treated. Plants may include, among others, legumes, herbs and root vegetables or leafy produce (for example, parsley). As used herein, the term "harvest" refers to the gathering of agricultural plant products, including picking (e.g. fruit), detaching from the ground (e.g. leafy crops such as lettuce, spinach and parsley), cutting (e.g. branches, including ornamental branches) and the like.

According to certain embodiments the ureide is selected from allantoin or allantoate.

According to some embodiments applying the composition to plants includes spraying the plants or plant parts with the composition. According to other embodiments applying includes adding the composition to the plant's root or plant's branch medium. According to further embodiments, the composition is applied by at least partially immersing the plant or plant part in the composition. A combination of applying methods may also be used according to embodiments of the invention.

Elevated ureide amounts within a plant cell may be achieved by selecting a variant plant or genetically engineering the plant to produce or accumulate higher ureide concentration as compared to a wild type plant. The selected or engineered plants can overexpress enzymes involved in the production pathway of urieds, or have decreased expression levels of ureide utilization enzymes such that ureide is accumulated. The selection for the plant may include using a probe specific for at least one enzyme related to the production or accumulation of urieds and/or selecting a mutant having enhanced purine turnover.

Thus, according to another aspect the present invention provides a plant having enhanced ureide production wherein the plant comprises a genetic variant of at least one enzyme in the pathway of ureide production from a xanthine.

According to another aspect, the present invention provides a plant having enhanced ureide accumulation wherein the plant comprises a genetic variant of at least one enzyme in the pathway of ureide utilization.

According to a further aspect the present invention provides a transgenic plant comprising at least one cell transformed with at least one polynucleotide encoding an enzyme in the pathway of ureide production from a xanthine. According to certain embodiments, the transgenic plant produces elevated concentration of ureide compared to a corresponding non-transgenic plant.

According to yet additional aspect the present invention provides a transgenic plant comprising at least one cell transformed with at least one polynucleotide encoding an enzyme in the pathway of ureide utilization. According to certain embodiments, the transgenic plant accumulates elevated concentration of ureide compared to a corresponding non-transgenic plant.

These and other embodiments of the present invention will become apparent in conjunction with the figures, description and claims that follow.

BRIEF DESCRIPTION OF THE FIGURES

FIG. 1a shows Atxdh1 and Atxdh2 relative expression monitored by quantitative real-time RT-PCR analysis using wild-type (Col, left panel) and XDH compromised plants (KO, SALK_148364 Atxdh1 T-DNA insertion line; and Ri, three xdh RNA interference lines, right panel). FIG. 1b shows XDH-dependent NADH oxidase and FIG. 1c shows XDH-dependent hypoxanthine/xanthine dehydrogenase activities in wild type (Col, left panel) and KO (XDH compromised plants, right panel) leaf extracts. The $O_2^-$ generated in-gel was measured using NBT as electron acceptor and presented relative to day 0 or, during the recovery period, relative to day 6 in the dark. Each lane contained 200 μg of soluble proteins. FIG. 1d demonstrates $O_2^-$ generating activity of XDH in leaf extracts of wild-type and XDH compromised plants. Plants were treated and sampled as described above. Kinetics was assayed using epinephrine as electron acceptor and hypoxanthine/xanthine as substrate following by adenochrome absorbance. Values are means±SE (n=6).

FIG. 2a shows wild-type (Col) and XDH compromised plants (KO, SALK_148364; Ri, xdh1 RNA interference) during 6 day dark treatment and subsequent 9 days recovery. FIG. 2b shows survival rates of wild-type and XDH compromised plants 15 days after exposure to the conditions described in FIG. 2a. Error bars indicate SE (n=12). FIG. 2c shows leaves of control untreated and dark-treated plants and XDH compromised plants excised before (0) and 6 days after (6) exposure to dark. FIG. 2d demonstrates the damage level of leaves shown in FIG. 2c calculated as described in the experimental procedures. Bars show means±SEM (n=6). FIG. 2e shows chlorophyll content in leaves sampled over a 6 day dark treatment. Error bars indicate SE (n=6). FIG. 2f shows total soluble protein content in leaves sampled over a 6 day dark treatment. Error bars indicate SE (n=6).

FIG. 4a demonstrates superoxide level as visualized by NBT staining of rosette leaves in the absence or presence of allopurinol (+Allo) or diphenylene iodonium (+DPI). FIG. 4b shows quantitative analysis of NBT-$O_2^-$ production in leaves in response to dark treatment. NBT-$O_2^-$ generation was quantified in stained leaves by scanning. Upper insert: total relative NBT-$O_2^-$ generation; middle insert: relative NBT-$O_2^-$ generation by XDH obtained by subtraction of +Allo from −Allo leaf scan values; lower insert: relative NBT-$O_2^-$ generation by non-XDH source, obtained by subtraction of +DPI from +Allo leaf scan values. Data are means±SE (n=8).

FIG. 7a shows 75 days old wild type (Col) and xdh1 RNA interference (Ri) plants and their representative leaves (left and middle panels). The transcript expression of SAG12 measured by quantitative real-time RT-PCR and normalized to the EF-1α transcript (At5g60390) is shown at the right panel. Values are means±SEM (n=6). Data for Ri lines are means of 3 independent lines. FIG. 7b shows concentration of the purine metabolites xanthine (left panel), allantoin (middle panel) and allantoate (right panel), measured in rosette leaves, in response to plant age. Values are means±SEM (n=6). FIG. 7c demonstrates transcript expression of *Arabidopsis* purine catabolism genes using wild-type (Col) and three independent Ri plants. The transcript expressions are relative to the level at 30 days and normalized to the EF-1α transcript (At5g60390). Values are means±SEM (n=3).

FIG. 8a: xanthine (1 mM) in the presence or absence of allopurinol (1 mM, +/−Allo), was applied for 48 h to leaf discs placed in the dark and photographed 24 h after being transferred to 16 h light/8 h dark regime (left upper panel). Remaining chlorophyll, xanthine, allantoin and allantoate were determined in leaf discs sampled at the beginning of the experiment (light) or after 72 h (as described above) without xanthine (dark). FIG. 8b: allantoin or allantoate (0.1 mM) in the presence or absence of allopurinol (1 mm, +/−Allo) was applied to leaf discs for 2 h in the dark after keeping the discs in the dark for 48 h. Discs were photographed 24 h after being transferred to 16 h light/8 h dark regime (left upper panel). Leaf discs were washed twice before sampling for xanthine, allantoin and allantoate determination (right and bottom panels). Bars show mean±SEM (n=16).

FIG. 9a left panel: leaf discs removed from Col plants placed for 24 h in the dark in the presence or absence of allantoin or allantoate (0.1 mM) and then washed and treated with $H_2O_2$ (0, 20, 50 mM) for an additional 6 h in the dark. Right panel: remaining chlorophyll determined 24 h after the disc were transferred to a 16 h light/8 h dark regime. Bars show mean±SEM (n=16). FIG. 9b shows $H_2O_2$ production in leaf discs of Col and Ri plants treated with allantoin or allantoate (0.1 mM) visualized by staining with 3,3'-diaminobenzidine (DAB) (left panel). Total $H_2O_2$ relative production (right insert) was quantified in leave discs kept in the dark for 24 h and then treated with allantoin or allantoate for additional 2 h in the dark, using DAB staining Results are from two independent experiments. Error bars indicate SE (n=16). The lower case letters (a, b) indicate P<0.001 for the differences within treatment between ecotypes. Capital letters (A, B) indicate P<0.001 for the differences within ecotypes between treatments. FIG. 9c demonstrates the influence of allantoin or allantoate (0.1 mM) on $O_2^-$ production in leaf discs of Col and Ri plants. Leaf discs were treated and analyzed as in FIG. 9b above. Total relative superoxide production was quantified in leaf discs from 2 independent experiments. Error bars indicate SE (n=16).

Parsley leaf discs were kept for 2 days in the light and then transferred to the dark for additional 2 days with or without the addition of 0 to 10 mM allantoin. CL—control undetached leaves in the light.

Figure 14:
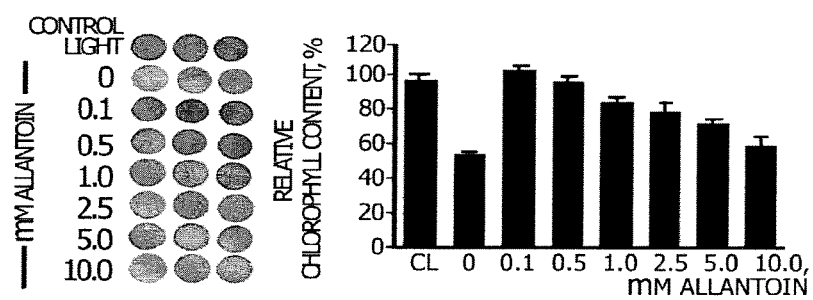
FIG. 14 relates to the influence of allantoin application on senescence in parsley leaf discs exposed to dark stress.
Figure 15A:
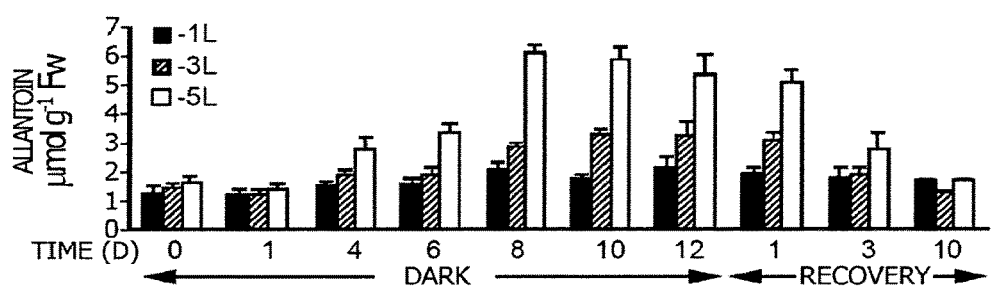
Figure 15B:
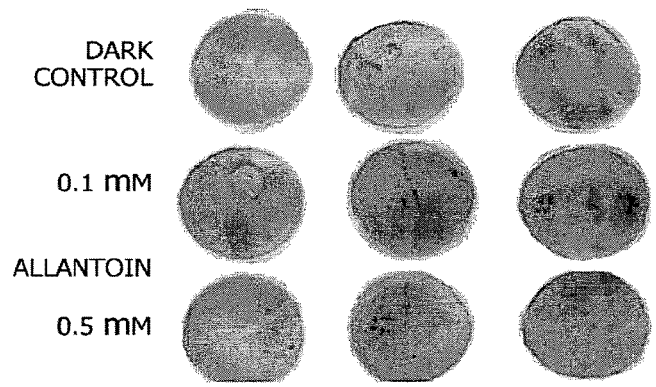

FIGS. 15a-b demonstrate the response of tomato to extended dark stress and recovery in light thereafter. FIG. 15a shows the allantoin level in the 1st, 3rd and 5th leaf of wild type tomato plants over a period of 12 days in the dark and 10 days of recovery in the light. FIG. 15b shows that application of 0.1 mM and 0.5 mM allantoin delays chlorophyll degradation in tomato leave discs (treated as in FIG. 14).

DETAILED DESCRIPTION OF THE INVENTION

The present invention provides compositions and methods for protecting plants and parts thereof from senescence and stress related processes. The present invention further provides compositions and methods for extending the shelf life of plant fresh produce including, but not limited to, herbs, vegetables, cut branches, fruit and flowers. Without wishing to be bound by any theory or mechanism of action, shelf life extension of the fresh produce according to the teachings of the present invention may be attributed to protection of the harvested material from processes such as senescence, premature senescence and stress related processes.

According to certain embodiments, the present invention relates to regulation of ureide levels for optimal plant survival during nutrient remobilization such as occurs during normal growth, dark stress, senescence and other plant processes.

According to some embodiments, plants can be genetically engineered or selected using a suitable gene marker to achieve enhanced ureide production and/or accumulation.

According to some embodiments the present invention identifies enzymes and enzyme variants that regulate the production of ureides in plants.

The present invention is based in part on the use of experimental models of plant senescence and stress such as extended dark treatment in order to induce metabolite remobilization processes. It is now disclosed for the first time that both dark-induced stress and increased age induce accumulation of ureides, including allantoin and allantoate, in wild-type leaves. In contrast under these conditions, in XDH1-compromised plants, xanthine but no ureides accumulate, and accelerated senescence and mortality rates are observed. Thus, a protective role for AtXDH1 and ureides in senescence is demonstrated.

Unexpectedly, this protection can also be achieved by the exogenous application of ureides. In particular, the present invention provides compositions and methods comprising exogenous ureides for protection of picked or harvested agricultural produce from processes, such as senescence and premature senescence.

According to a first aspect, the present invention provides a method for protecting plants, plant parts or harvested plant produce from aging (for example, senescence or premature senescence). According to one embodiment, the method comprises applying to the plant(s) or plant part(s) a composition comprising an amount of at least one ureide effective to decrease or delay the senescence of the plant or plant parts. According to some embodiments the ureide is selected form allantoin or an allantoate.

According to one embodiment plants or plant parts may be selected from harvested herbs, fruits, vegetables and flowers.

In particular, the present invention provides compositions and methods for protecting harvested agricultural produce from typically stress related processes such as senescence and premature senescence. Picked flowers and leafy crops such as lettuce, spinach, parsley and many others typically begin to undergo senescence immediately after they are picked. This process is typically accelerated during storage of the plant produce. Typically, this means that the green leafy tissue yellows and its nutritional and marketing value may decrease. Embodiments of the present invention thus disclose that the exogenous application of ureides slows this progress and extends plant produce shelf life.

Methods, according to some embodiments of the invention, may comprise applying, such as by applying to the root or cut branches medium or spraying, a composition which includes an appropriate amount of ureides onto the produce or immersing or partially immersing the produce in a suspension or other appropriate form of composition containing ureides or purine metabolites such as uric acid. Any suitable application method, such as, but not limited to, the methods listed here, may be used alone or in combination. According to some embodiments any solution comprising ureides in the range of 1 µM-10 mM may be used. Typically a solution in a range of 0.01-10 mM, or 0.1-10 mM is used. Any concentration of ureides in the specified ranges may be used. According to one embodiment 0.1 mM ureide, 0.5 mM ureide or any concentration of ureides in this range may be used. Compositions having other concentrations may also be used with embodiments of the invention.

As exemplified hereinbelow application of exogenous ureides protects plants and plant parts from senescence and stress related processes.

According to another aspect of the invention ureide accumulation may be enhanced in genetically engineered plants. In the alternative, plants may be genetically engineered to achieve enhanced and optimal ureide production. Expression of enzymes specifically required in the pathway of ureide production may be optimized, according to one embodiment of the invention, in order to achieve ureide accumulation. According to further aspects the present invention provides a plant selected for enhanced ureide production. According to one aspect a genetically modified plant can be obtained by enhancing expression levels of enzymes involved in the production pathway of ureides thereby increasing ureide production. According to another aspect a genetically modified plant can be obtained by decreasing expression levels of ureide utilization enzymes by genetic engineering thereby increasing ureide accumulation.

According to another aspect the desired plant can be selected using a probe specific for at least one enzyme related to the production or accumulation of ureides. According to one embodiment the desired plant can be selected using a probe specific for XDH encoding gene or XDH enzyme expression.

According to one embodiment a genetically modified plant is selected for mutations for enhanced purine turnover. A specific controlling element may up and down regulate purine catabolic pathways synchronously, i.e. up regulate the enzymes that make ureides and simultaneously down-regulate the enzymes that can breakdown the ureides. Such selection can be done by various known mutational methods e.g., subjecting plants to mutagenesis as in enhancer trap methods, irradiation, chemical mutagenesis, insertional mutagenesis and other appropriate methods. According to one embodiment an enhancer is inserted randomly in the genome and the resultant lines are screened for changes in ureide levels. According to various embodiments generic lines may be used for screening of ureide production.

According to another aspect identification of transcripts relevant to the ureide metabolism (production or degradation) can be used to perform large scale screening for natural variations in ureide levels in plants in response to stress. According to a particular embodiment the natural variants in ureide levels are screened during or after extended dark periods.

It should be understood that composition and/or methods according to embodiments of the invention may be used alone or in combination to achieve results according to the invention. For example, several different concentrations and/or different ureides may be applied to plant, plant parts or crops, according to embodiments of the invention. Genetic engineering and/or screening methods may be used in combination with methods of applying ureides to plants. Any combination of the methods and/or compounds disclosed herein, which achieves protection of plants through the ureide metabolic pathway, is disclosed herein.

The remobilization of metabolites during stress and senescence plays an important role in optimal plant adaptation to the environment. The plant molybdenum-cofactor (MoCo) and flavin containing enzyme, xanthine dehydrogenase (XDH; EC 1.2.1.37) are pivotal for purine remobilization and catalyze the conversion of the purine catabolic products, hypoxanthine and xanthine to uric acid that is subsequently degraded to the ureides, allantoin and allantoate. The present invention now shows that in wild-type plants, conditions of extended darkness or increasing leaf age cause induction of transcripts related to purine catabolism, that in turn result in marked accumulation of the purine catabolic products, allantoin and allantoate. In contrast, *Arabidopsis* mutants of XDH, Atxdh1, accumulated xanthine and showed premature senescence symptoms as exemplified by enhanced chlorophyll degradation, extensive cell death and up-regulation of senescence-related transcripts. When dark-treated mutant lines were re-exposed to light, they showed elevated levels of reactive oxygen species (ROS) and higher mortality rate compared to wild-type plants. Unexpectedly, the level of ROS and mortality could be attenuated by the addition of allantoin and allantoate suggesting that these metabolites can act as scavengers of reactive oxygen species. The present invention highlights a yet unrecognized need for the controlled maintenance of ureide levels, for example, as mediated by AtXDH1 activity during dark stress and ageing and point to the dual functionality of ureides as efficient stores of nitrogen and as cellular protectants. Thus, regulation of ureide levels by regulating Atxdh1 expression has general implications for optimal plant survival during nutrient remobilization such as occurs during normal growth, dark stress and senescence.

XDH1 Activity Moderates Pre-Mature Senescence Induced by Dark Stress

Extended dark treatment implies complete lack of new photosynthesis that imposes a stress which requires remobilization of leaf resources. In this sense, extended dark initiates molecular events that are reminiscent of leaf senescence. The progression of senescence must be orderly so that the accumulation of deleterious compounds or physiological states of enhanced labile cellular state is avoided. It is shown here that XDH1 activity is required for normal remobilization to succeed, as in its absence, not only will direct purine catabolism be compromised, but the rate of chlorophyll, soluble protein degradation (FIGS. 2e and 2f) and cell death are all accelerated.

Figure 2A:
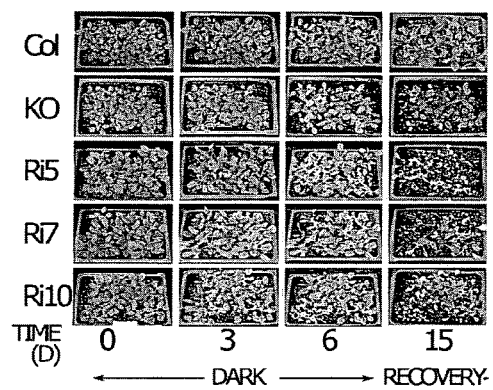
FIGS. 2a-2f demonstrate the responses of wild-type and XDH compromised *Arabidopsis* plants to dark stress.
Figure 2B:
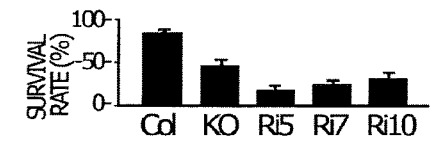
Figure 2C:
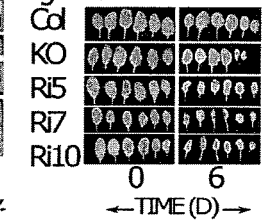
Figure 2D:
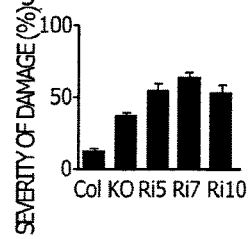
Figure 2E:
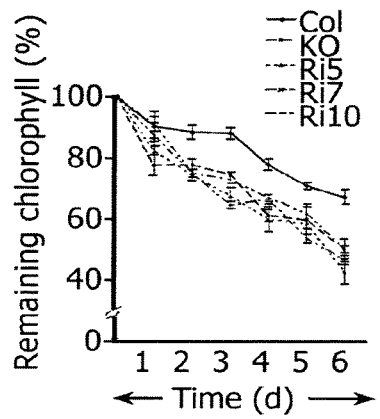
Figure 3:
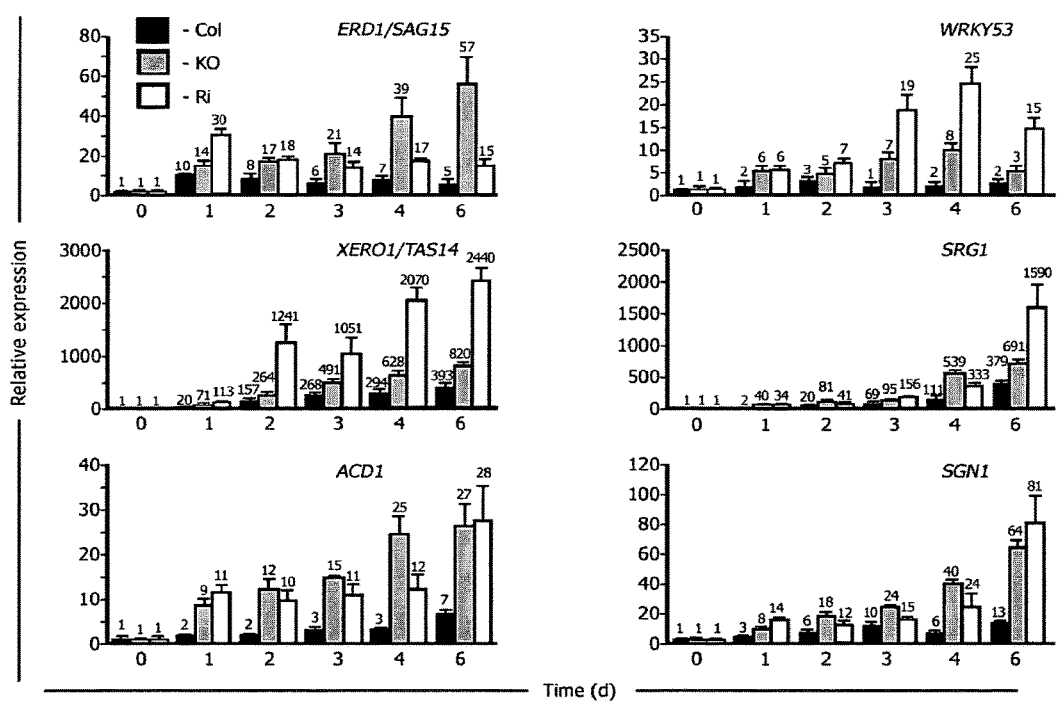
FIG. 3 demonstrates relative transcript expression of selected senescence and chlorophyll degradation-related genes. Transcripts were monitored by quantitative real-time RT-PCR analysis using wild-type (Col) and XDH compromised plants (KO, SALK 148364, Atxdh1 T-DNA insertion line and Ri, mean of 3 independent xdh1 RNA interference lines). Plants were sampled before being placed in the dark (0) and over a dark period of six days. The transcript expressions of each treated line was compared to the untreated line after normalization to the *Arabidopsis* EF-1α gene product (At5g60390) and presented as relative expression. Values are means±SEM (n=6).

The value of extended dark treatments as a signal that stimulates synchronized metabolic remobilization in the plant was discerned by examining transcript induction profiles of genes that are known to be induced during senescence. For example, the WRKY53 transcription factor (which was shown to control early events of senescence and oxidative stress response (Miao Y. et al., 2004 Plant Mol Biol 55, 853-867). The protease regulator, ERD1 encodes caseinolytic protease regulatory subunit, and may be related to posttranslational modification processes, as it was shown to be involved in the degradation of chloroplast proteins subjected to artificial senescence related to ABA, ethylene and $SO_2$ (Brychkova G. et al., 2007 Plant J 50, 696-709; Weaver L. M. et al., 1998 Plant Mol Biol 37, 455-469). Similarly, chlorophyll degradation (Gepstein S. 2004 Genome Biology 5, 212; Pruzinska A. et al., 2005 Plant Physiol 139, 52-63) and up-regulation of related transcripts such as ACD1 and SGN1 (Park S. Y. et al., 2007 Plant Cell 19, 1649-1664; Tanaka R. et al., 2003 Plant Cell Physiol 44, 1266-1274), during the extended dark period are indicative of leaf senescence. The up-regulation of the chlorophyll-degradation related transcripts and chlorophyll degradation itself is a hallmark of compromised XDH1 activity (FIG. 2e and FIG. 3, lower panels). Thus, as indicated by these marker genes, the presence of XDH1 activity affords wild-type plants protection from the onset of program cell death-like process during the dark stress.

XDH Activity in Response to Dark Stress

Figure 11:
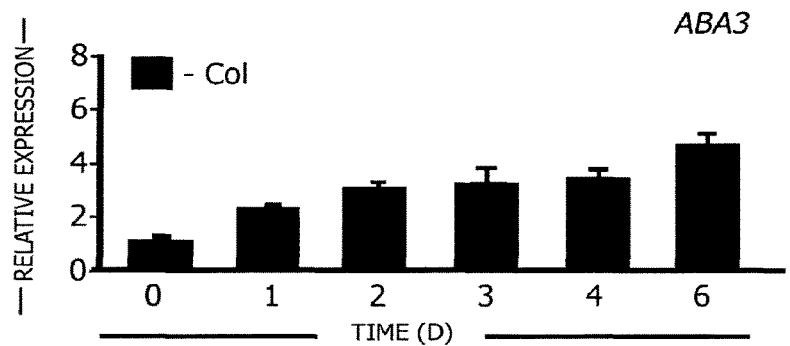
FIG. 11 shows transcript expression of the *Arabidopsis* molybdenum cofactor sulfurase gene, ABA3, in wild type (Col) plants after exposure to dark stress for six days. Transcript Analysis was performed as described in FIG. 10 above.

XDH possesses a MoCo sulfurated-dependent hypoxanthine/xanthine-O2-generating activity and a FAD dependent $NADH-O_2^-$-generated activity (Sagi M. et al., 1999 Plant Physiol 120, 571-578; Sagi M. et al., 2002 Plant J 31, 305-317; Yesbergenova Z. et al., 2005 Plant J 42, 862-876). The xanthine-dependent superoxide generating activity was more enhanced in extended dark than the NADH-dependent activity (FIGS. 1b-1d and FIG. 4b middle panel). This indicates that modification processes involving the MoCo-domain are likely taking place during the dark-derived remobilization. Difference between MoCo and FAD dependent activities of XDH may result from interconversion of the sulfo- and desulfo-MoCo forms of XDH. The terminal sulfuration step carried out by the MoCo-sulfurase enzymes FLACCA in tomato and ABA3 in *Arabidopsis* were hypothesized to provide an efficient way to regulate XDH activities by sulfuration (Sagi et al., 1999, ibid; Sagi et al., 2002 ibid). XDH commonly contains significant portions of desulfo-forms, which while inactive in hypoxanthine/xanthine oxidases (Harrison R. 2002 Free Radic Biol Med 33, 774-797), are active as NADH oxidases (Yesbergenova et al., 2005, ibid). Thus, the enhancement in hypoxanthine/xanthine oxidase activity observed in dark-induced stress may result from enhanced sulfuration status of the XDH MoCo domain. Consistent with this scenario, it is noted that the ABA3 transcript was significantly enhanced during dark stress (about 3-fold; FIG. 11).

Role of Purine Catabolism in Dark Stress and Recovery

Figure 5A:
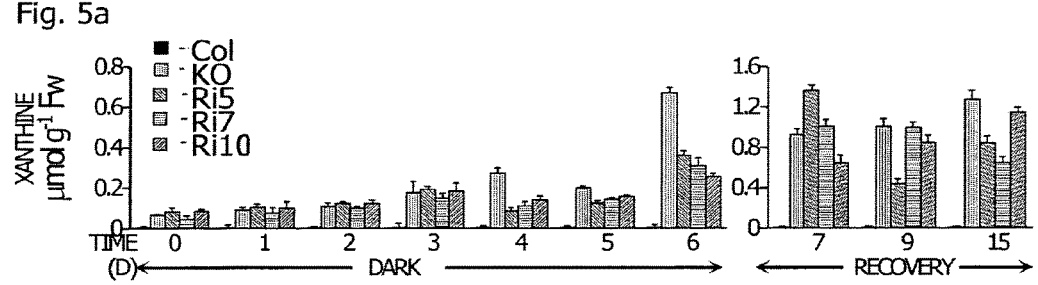
FIGS. 5a-5c show analysis of the purine metabolites, xanthine, allantoin and allantoate, in response to dark stress. Xanthine (FIG. 5a), Allantoin (FIG. 5b) and Allantoate (FIG. 5c) were determined in rosette leaves of wild-type (Col) and XDH1 compromised plants (KO, SALK 148364; Ri, xdh1 RNA interference) after being kept in dark for 6 days and transferred to 16 h light/8 h dark regime for recovery during additional 9 days. Values are means±SEM (n=6).
Figure 8A:
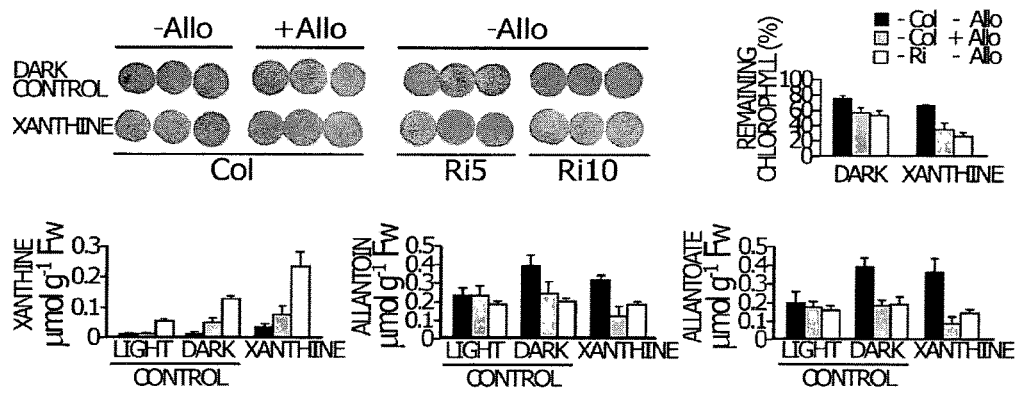
FIGS. 8a-8b demonstrate the responses of *Arabidopsis* wild-type (Col) and xdh RNA interference (Ri) plants to application of the purine catabolites: xanthine, allantoin and allantoate.
Figure 8B:
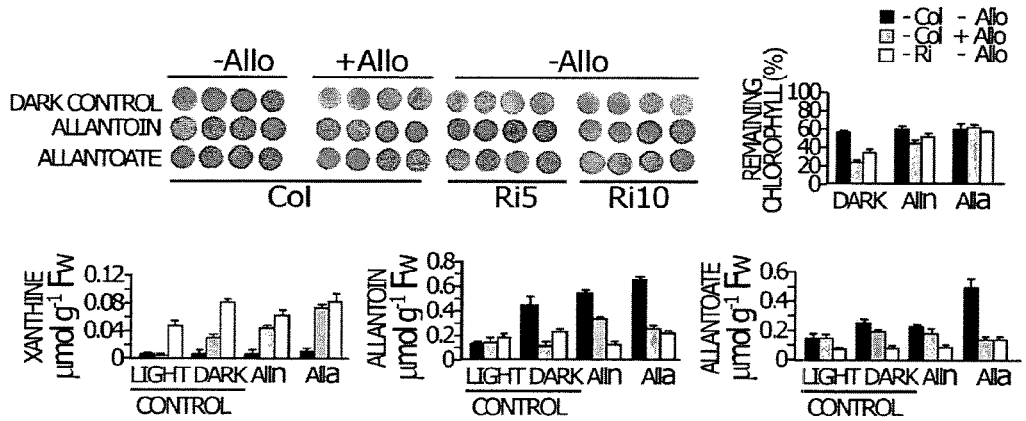

Mutation in AtXDH1 or application of allopurinol to wild type plants led to xanthine accumulation during dark stress (FIGS. 5a and 8a, 8b). The degree of tissue damage that appears in plants during the dark and especially during the subsequent light treatment may be due to direct or indirect sensitivity to excess xanthine, leading to chlorophyll degradation, especially in the absence of active AtXDH1 in the treated leaves (FIG. 8a). However, the higher chlorophyll degradation that appeared in mutant leaves containing high level of xanthine was significantly alleviated by the addition of allantoin and allantoate implying that ureides protected leaves from dark induced chlorophyll degradation in spite of xanthine accumulation (FIG. 8b). Thus, ureides accumulation may contribute to the cell normal growth pattern through a critical physiological state brought upon by metabolite remobilization. Hence, ureides represent both favorable N—C ratio as well as molecules with an intrinsic ability to scavenge ROS excess. Such excess may be encountered during re-exposure of leaves to light in which photosystem imbalance may be the end result of enhanced protein turnover that results in transient light-dependent ROS production.

A coordinated rise in transcripts level involved in ureide production (AMPD, XDH1, UO and TLP) and a concomitant decrease in transcripts level of enzymes that utilize ureides (ALN and AAH) was detected. Thus, dark stress ureides accumulation is at least in part under transcriptional control and is likely to result from the difference in activities involved in ureides formation versus the activities that process them.

Figure 13:
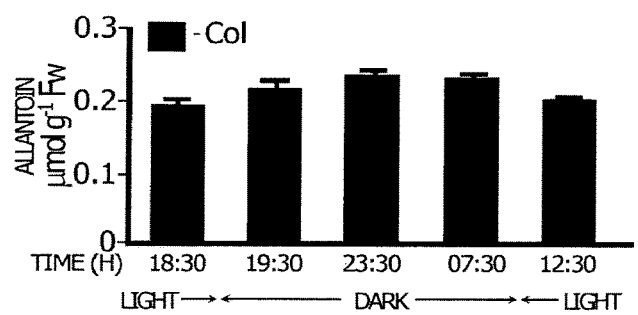
FIG. 13 shows diurnal fluctuation of allantoin in rosette leaves of wild-type (Col) *Arabidopsis* plants. Values are means±SEM (n=6).

The data presented in the present invention have highlighted a complete and functional purine remobilization pathway that occurs in the extended absence of light but the implications are not restricted to conditions of environmental stress. Rapid XDH1 up-regulation (FIGS. 1a and 1c) and a mild increase in ureide levels in normal diurnal light dark transitions (22%; FIG. 13) are noted. The diurnal cycling of ureide levels indicates that extended dark treatment accentuates a normal response. In this respect, the physiological and molecular components of dark-induced stress are shown here to be reminiscent of normal leaf ageing and senescence. Indeed in dark stress and senescence similar levels of ureides accumulation was shown (FIGS. 5 and 7).

Senescence and dark-induced senescence are associated with modulation of ROS production (Guo F. Q. and Crawford N. M. 2005 Plant Cell 17, 3436-3450; Pastori G. M. and Del Rio L. A. 1997 Plant Physiol 113, 411-418). Thus, without wishing to be bound by any particular theory opr mechanism of action, ureides may serve a dual function in senescence as transportable metabolites for further biosynthetic pathways and at the same time as cellular protectants from ROS. The results herein show that purine catabolism, ageing and extended dark induce similar senescence programs. In both cases, the transition from nutrient assimilation to metabolite turnover occurs due to the acceleration of purine catabolic recycling activities in which AtXDH1 plays a pivotal role.

Examples of specific experiments carried out on specific plants are presented herein in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Experimental Procedures

Plant Materials, Growth Conditions and Dark Treatment

*Arabidopsis thaliana* (ecotype Columbia) and its isogenic Atxdh1 compromised plants were grown in a growth room under 16 h light/8 h dark, 22° C., 75-85% relative humidity, light intensity of 100 μmol m$^{-2}$ s$^{-1}$ as described before (Brychkova G. et al., 2007, ibid). Atxdh1 compromised plants included homozygous T-DNA inserted line [SALK_148364 (obtained from the *Arabidopsis* Biological Research Center, Columbus, Ohio, USA)] and 3 independent homozygous xdh RNA interference lines described before (Yesbergenova et al., 2005, ibid). For dark treatment, four-week-old plants grown in peat were transferred from the growth room to a dark room. Samples were collected every day during 15 min, under dim light (40 μl, mol m−2 s−1), as a mix of fully expanded rosette leaves taken from 5 plants. After 6 days in the dark, plants were transferred to the growth room and survival rate of plants were determined 9 days later. Average and S.E. of survival rate was calculated from 12 independent experiments with at least 30 plants for each treatment. For aging measurements plants were grown in a growth room as described above and samples were collected from 30, 45, 60 and 75 day old plants as a mix of fully expanded rosette leaves taken from 5 plants.

Cell Death Measurements, Determination of Chlorophyll and Leaf Damage Level

Cell death was visualized in leaves sampled from dark stressed and control unstressed plants, by lactophenol-trypan blue staining followed by destaining in saturated chloral hydrate (Koch E. and Slusarenko A. 1990 Plant Cell 2, 437-445). Total chlorophyll content was measured in extracts of the fully expanded leaves as described before (Brychkova et al., 2007, ibid). The values for remaining chlorophyll content in leaf discs were determined as the amount of chlorophyll per disc divided by the amount of chlorophyll per untreated control and expressed as a percentage. The severity of leaf damage after dark stress was as follows: 1, no damage; 2, <30%; 3, 30-50%; 4, >50% of the leaf area damaged. The average leaf damage was then multiplied by the total number of damaged leaves to determine the damage level. Means±SEM for each treatment are presented.

Preparation of RNA and Quantitative Real-Time RT-PCR

For quantitative analysis of transcripts expression, total RNA, RT reaction and quantitative RT-PCR reactions with specific primers (see Table 1 hereinbelow) were performed as describes in Brychkova et al. (2007, ibid). Reactions normalized with UBQ10 (At4g05320) and Elongation factor 1-α (At5g60390) as housekeeping genes revealed similar results and thus only results based on the later housekeeping gene are presented.

TABLE 1

List of primers used for quantitative real-time PCR with *Arabidopsis thaliana*

| PCR product | Primer | Length of PCR Transcript |
|---|---|---|
| SGN1 (StayGreen1; | Forward GATTGTTCCCGTTGCAAGGTTGTTT | 189 |

TABLE 1-continued

List of primers used for quantitative real-time PCR with *Arabidopsis thaliana*

| PCR product | Primer | Length of PCR Transcript |
|---|---|---|
| At4g22920) | (SEQ ID NO: 1) reverse TGCAACTGAGAGTTGTTTATGGATTGAG (SEQ ID NO: 2) | |
| SRG1 (senescence-related gene 1; At1g17020) | forward AAGAGTGGGGATTTTTCCAGCTTGT (SEQ ID NO: 3) reverse TGCCCAATCTAGTTTCTGATCTTCTGA (SEQ ID NO: 4) | 191 |
| UBQ10 (Ubiquitine10; At4g05320) | forward TTTGTTAAGACTCTCACCGGAAAGACA (SEQ ID NO: 5) reverse GAGGGTGGATTCCTTCTGGATATTGTA (SEQ ID NO: 6) | 192 |
| UO (Urate oxidase; At2g26230) | forward CACTGTTTATGTGAAAGCCAAGGAATG (SEQ ID NO: 7) reverse CCCAAGCTTAAAACCATGTAAATGTGG (SEQ ID NO: 8) | 187 |
| TLP (transthyretin-like protein; AT5g58220) | forward CCATGCGTTAAAGGAAAGGTATGAAAA (SEQ ID NO: 9) reverse TGATTCTCAGACGATCTTGAGGTTTTG (SEQ ID NO: 10) | 185 |
| WRKY53 (WRKY DNA-binding protein 53; At4g23810), | forward TCAAAGAAAAGAAAGATGTTACCAAAGTGG (SEQ ID NO: 11) reverse GTGCATCTGTAATAACTCCTTGGGAAT (SEQ ID NO: 12) | 158 |
| XDH1 (xanthine dehydrogenase 1; At4g34890) | forward TGATGTTGGACAAATAGAAGGAGCGTTT (SEQ ID NO: 13) reverse TATTCGGATTCCCCTTGAGAAGCGAAACA (SEQ ID NO: 14) | 200 |
| XDH2 (xanthine dehydrogenase 2; At4g34900) | Forward TGATATTGGACAAATAGAAGGAGCGTTT (SEQ ID NO: 15) reverse TGCATTTGGATTACCCTTGAGAAGAGAAA (SEQ ID NO: 16) | 202 |
| XERO1/TAS14 (dehydrin; At3g50980) | forward AGACTCACCAACAGCTTGACCAATTT (SEQ ID NO: 17) reverse CACCTAGTCCATCATCCGAGCTAGAG (SEQ ID NO: 18) | 165 |
| SGN1 (StayGreen1; At4g22920) | Forward GATTGTTCCCGTTGCAAGGTTGTTT (SEQ ID NO: 19) Reverse TGCAACTGAGAGTTGTTTATGGATTGAG (SEQ ID NO: 20) | 189 |

TABLE 1-continued

List of primers used for quantitative real-time PCR with *Arabidopsis thaliana*

| PCR product | Primer | Length of PCR Transcript |
|---|---|---|
| SRG1 (senescence-related gene 1; At1g17020) | forward AAGAGTGGGGATTTTTCCAGCTTGT (SEQ ID NO: 21) reverse TGCCCAATCTAGTTTCTGATCTTCTGA (SEQ ID NO: 22) | 191 |
| UBQ10 (Ubiquitine10; At4g05320) | forward TTTGTTAAGACTCTCACCGGAAAGACA (SEQ ID NO: 23) reverse GAGGGTGGATTCCTTCTGGATATTGTA (SEQ ID NO: 24) | 192 |
| UO (Urate oxidase; At2g26230) | forward CACTGTTTATGTGAAAGCCAAGGAATG (SEQ ID NO: 25) reverse CCCAAGCTTAAAACCATGTAAATGTGG (SEQ ID NO: 26) | 187 |
| TLP (transthyretin-like protein; AT5g58220) | forward CCATGCGTTAAAGGAAAGGTATGAAAA (SEQ ID NO: 27) reverse TGATTCTCAGACGATCTTGAGGTTTTG (SEQ ID NO: 28) | 185 |
| WRKY53 (WRKY DNA-binding protein 53; At4g23810), | forward TCAAAGAAAAGAAAGATGTTACCAAAGTGG (SEQ ID NO: 29) reverse GTGCATCTGTAATAACTCCTTGGGAAT (SEQ ID NO: 30) | 158 |
| XDH1 (xanthine dehydrogenase 1; At4g34890) | forward TGATGTTGGACAAATAGAAGGAGCGTTT (SEQ ID NO: 31) reverse TATTCGGATTCCCCTTGAGAAGCGAAACA (SEQ ID NO: 32) | 200 |
| XDH2 (xanthine dehydrogenase 2; At4g34900) | Forward TGATATTGGACAAATAGAAGGAGCGTTT (SEQ ID NO: 33) reverse TGCATTTGGATTACCCTTGAGAAGAGAAA (SEQ ID NO: 34) | 202 |
| XERO1/TAS14 (dehydrin; At3g50980) | forward AGACTCACCAACAGCTTGACCAATTT (SEQ ID NO: 35) reverse CACCTAGTCCATCATCCGAGCTAGAG (SEQ ID NO: 36) | 165 |

Histochemical Staining for $O_2^-$ and $H_2O_2$ Detection

Nitroblue tetrazolium (NBT) $O_2^-$ staining of leaves was performed essentially according to Jabs T. et al. (1996 Science 273, 1853-1856) and Fryer M. J. et al. (2002 J Exp Bot 53, 1249-1254). Leaves were incubated for 10 h in the dark overnight and then placed in 96% ethanol, boiled for 10 min and photographed. Application of allantoin and allantoate and $O_2^-$ and $H_2O_2$ measurement was carried out on 7 mm leaf discs removed from 4-week-old Col wild-type and Atxdh1 mutant plants. Discs were placed in the dark for 24 h on moistened filter papers. Thereafter, 0.1 mM allantoin or allantoate in pH 7.5 solution was added to the filter papers for additional 2 h. For NBT-$O_2^-$ staining, leaf discs were washed twice and immersed in 0.8 mM NBT solution added to the filter papers for 2 h in the light and then boiled in 96% ethanol for 10 min and photographed. For DAB-$H_2O_2$ staining leaf discs subjected to the procedure described above for NBT were immersed in solution containing 1 mg ml$^{-1}$ 3,3'-diaminobenzidine (DAB) in pH 5.0, for 2 h in the light as described before (Sagi M. et al., 2004 Plant Cell 16, 616-628). Leaf discs were photographed after boiling in 96% ethanol for 10 min. NBT and DAB stained leaves and leaf discs were quantified using NIH Image Software (Version 1.6).

Protein Extraction, Fractionation and Total Soluble Protein Determination in-Gel and Kinetic Assay of ROS-Generating Activities of XDH Extracts of XDH for assay by native gel electrophoresis (PAGE) were prepared as described by Sagi M. et al. (1998 Plant Science 135, 125-135) and Yesbergenova et al. (2005, ibid). Kinetic $O_2^-$ generating activities of XDH were assayed spectrophotometrically by measuring the oxidation of epinephrine to adrenochrome at 480 nm as described previously in Sagi M. and Fluhr R. (2001 Plant Physiol 126, 1281-1290). The reaction medium contained 6.2 μg of protein extract, 1 mM epinephrine in 50 mM Tris-HCl buffer (pH 8.5) and 1 mM hypoxanthine/xanthine. Reaction medium without hypoxanthine/xanthine was used as control. Six samples were analyzed and averaged for each data points. Means±SEM for each treatment are presented.

Ureides, Hypoxanthine and Xanthine Determination

Ureides were extracted from leaves with 80% ethanol and determined according to Vogels G. D. and Van Der Drift C. (1970 Anal Biochem 33, 143-157) using allantoic acid and allantoin as references. Six samples were analyzed and averaged for each data points. For hypoxanthine and xanthine determination, leaves were extracted with 40 mM NaOH and diluted four times by Tris-HCl 0.1 M, pH 7.5. Hypoxanthine/xanthine were determined by high performance liquid chromatography (HPLC) using a 100×2.1 mm ID, ODS-Hypersil (5 μm) column. The mobile phase was a 10 mM NaOH/0.1 mM Tris-HCl, pH 5.0, similar to that used by Corpas F. J. et al., (1997 J Plant Physiol 151, 246-250). The hypoxanthine and xanthine were detected using standards retention time and UV absorption spectra ratio at 249 nm and 267 nm. A modified protocol to detect xanthine via the xanthine oxidase assay was used (Mohanty J. G. et al., 1997 Journal of Immunological Methods 202, 133-141). The reaction mixture modified from Yesbergenova et al., (2005 ibid), contained 0.4 U ml$^{-1}$ HRP, 40 mU ml$^{-1}$ buttermilk xanthine oxidase (Fluka), 3.4 mM 3,5-dichloro-2-hydroxobenzene sulphonate and 0.85 mM 4-aminoantipyrine in Tris-HCl 0.1 M, pH 7.5.

Figure 1A:
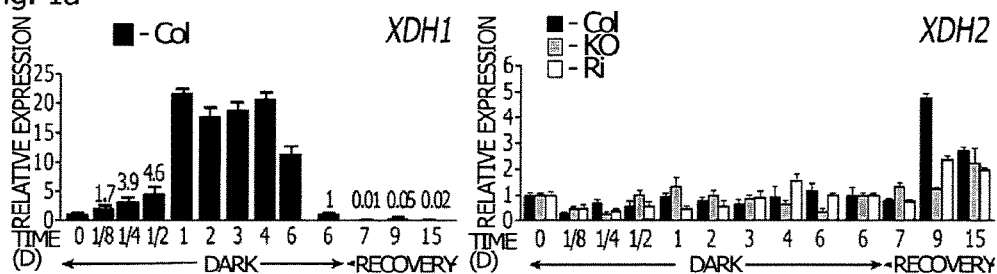
FIGS. 1a-1d demonstrate XDH expression in *Arabidopsis* wild type and Atxdh1 modified plants.
Figure 1B:
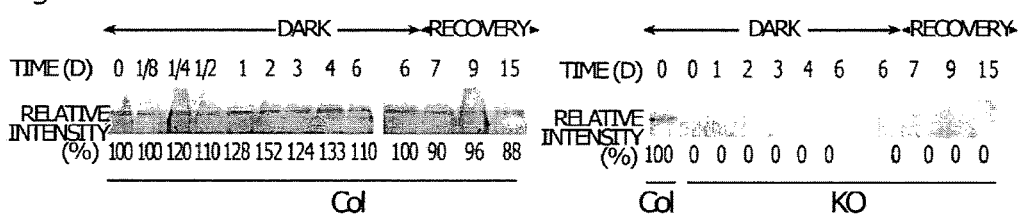

Example 1: XDH Expression During Dark-Induced Stress and its Subsequent Recovery XDH1 expression was examined under extended dark treatment that imposes major remobilization of cellular components. To this end, wild type Col plants and Atxdh1-compromised plants (RNA interference lines Ri5, Ri7 and Ri10; T-DNA insertion line, KO) impaired in XDH1 activity (Yesbergenova et al., 2005, ibid), were exposed to 6 days continuous dark followed by a 'recovery' period of 9 days under normal diurnal light regime (16 h light/8 h dark). The level of XDH1 transcript was found to increase continuously in the dark reaching a peak (>20 fold induction) in 24 h (FIG. 1a, left panel). The results imply that dark induction of XDH occurs as part of a normal diurnal physiological response although it rises to higher levels during the extended dark period. Upon return to light on the 7th d the transcript level rapidly decreased (FIG. 1a, left panel). In contrast, XDH2 transcript was unchanged during the dark treatment although it was slightly enhanced during the recovery period in both Col and the modified plants (FIG. 1a, right panel).

Example 2: XDH Superoxide Activity Parallels XDH Expression

Figure 1C:
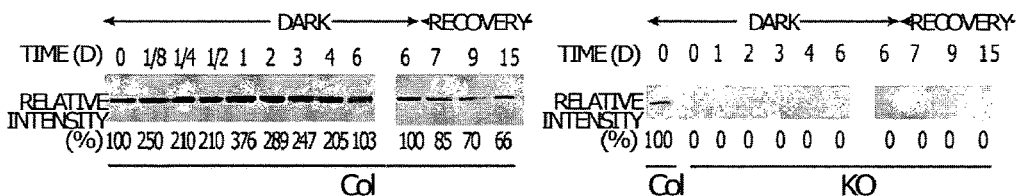
Figure 1D:
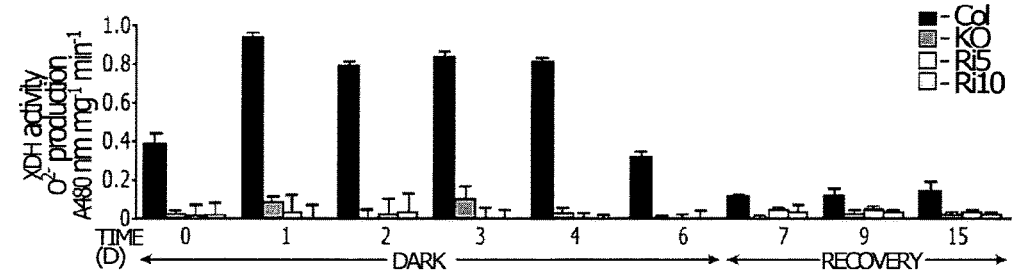

To ascertain whether potential enzymatic performance parallels the measured transcript changes, the in-gel activities of superoxide generation by XDH were tested using NADH and hypoxanthine/xanthine substrates (Yesbergenova et al., 2005, ibid). NADH-dependent activity exhibited at most a 1.5-fold enhancement in $O_2^-$ production during the dark period (FIG. 1b, left panel), whereas the hypoxanthine/xanthine-dependent activity increased immediately in the dark to nearly 3-fold levels at its maximum (FIG. 1c, left panel). No NADH-dependent or hypoxanthine/xanthine-dependent XDH activities were detected in Atxdh1 mutants (FIGS. 1b and c, right panels; data not shown for RNAi plants) even during the recovery period where XDH2 transcript was observed to increase (FIG. 1a). This could indicate that XDH2 activity or abundance is very low and demonstrates that typically XDH1 plays a role in dark stress adaptation. The results of the in-gel assay could be confirmed in a direct crude leaf extract assay using epinephrine as electron acceptor (Yesbergenova et al., 2005, ibid; FIG. 1d). In this case, at least a 2-fold increase in XDH activity could be detected in wild type leaves while mutant lines showed no or negligible activity. In all, while the exact fold level changes in activity differ according to the procedure used, the measured activities followed the general rise and fall in transcript levels.

Figure 2F:
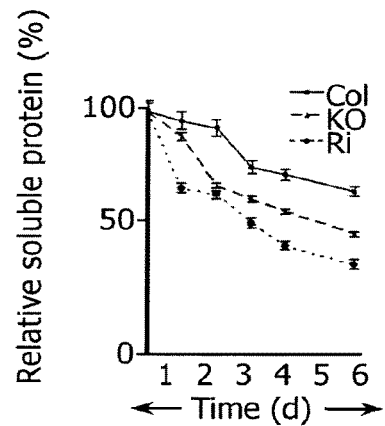

Example 3: Mutation in XDH1 Accelerates Premature Senescence in Dark-Induced Stressed Plants Reference is now made to FIG. 2, in which responses of wild-type and XDH compromised *Arabidopsis* plants to dark stress is shown. In FIG. 2a, wild-type (Col) and XDH compromised plants (KO, SALK 148364; Ri, xdh1 RNA interference) were tested during 6 day dark treatment and subsequent 9 days recovery. FIG. 2b shows survival rates of wild-type and XDH compromised plants 15 days after being exposed to the conditions described above. Leaves from control untreated and dark-treated Col and Atxdh1 compromised plants were excised before (0) and 6 d after (6) exposure to dark. FIG. 2d shows damage level of leaves. FIG. 2e shows chlorophyll content in leaves over a 6 d dark treatment FIG. 2f shows total soluble protein content in leaves over a 6 d dark treatment.

Figure 2G:
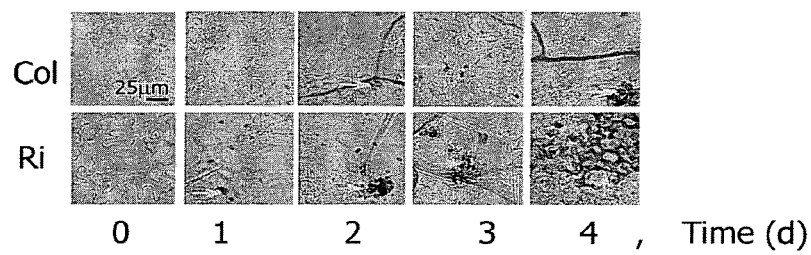
FIG. 2g demonstrates the progress in cell death over a 4 day dark treatment as indicated by staining with trypan-blue. At least 8 leaves were examined for each condition, and representative fields having the same magnification are shown.

Wild type Col and XDH1-compromised lines were examined more closely during the dark treatment. Rosette leaves of the mutant plants impaired in XDH1 expression were distinctly more yellow than wild type leaves (FIG. 2a, c). Quantitative analysis showed a rapid fall in residual chlorophyll levels of 30% and 50% in wild type and mutant leaves, respectively (FIG. 2e). The yellowing was accompanied by a reduction in soluble proteins, another hallmark of senescence (FIG. 2f). Atxdh1-compromised leaves compared to wild type leaves showed a higher damage rate (FIG. 2d) and accumulation of many more dead cells as ascertained by trypan blue staining (FIG. 2g). The plants were then returned to a normal diurnal cycle and their subsequent recovery was followed for an additional 9 days period. Wild-type plants showed an 80% survival rate as compared to 20 to 45% for the mutant lines (FIG. 2b). The results imply that XDH1-dependent processes are important for plant adaptation to extended dark treatment and subsequent recovery in normal light.

Example 4: Senescence and Chlorophyll Degradation-Associated Gene Expression in Atxdh1 Down-Regulated Plants Reference is now made to FIG. 3 in which transcripts were monitored by quantitative real-time RT-PCR analysis using wild-type (Col), XDH compromised plants (KO, SALK_148364, Atxdh1 T-DNA insertion line) and Ri (mean of 3 independent XDH1 RNA interference lines).

Figure 10:
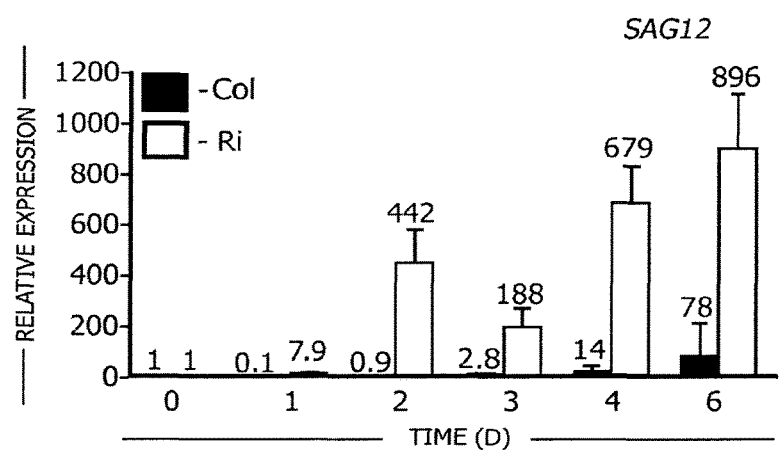
FIG. 10 shows transcript expression of the *Arabidopsis* Cys protease senescence-associated gene 12 (SAG12), during 6 days of dark stress. Quantitative analysis of transcript by real-time RT-PCR was performed using wild-type (Col) and three independent RNA interference (Ri) lines. Plants were sampled before dark application (0) and over the six days dark period. The expressions of each treated line were compared to those of the untreated line after normalization to the *Arabidopsis* EF-1α gene product (At5g60390) and data are presented as relative expression. Values are means±SEM (n=6). Data for Ri lines are means of 3 independent lines.

Enhanced dark-induced leaf yellowing in the mutant lines (such as that described in FIG. 2) may be indicative of hastened senescence. To examine this at the molecular level, the expression of early and late senescence-associated gene classes was monitored. Dark stress led to more rapid and enhanced accumulation of the early senescence transcripts, WRKY53 (senescence-related regulatory gene) and ERD1/SAG15 (senescence-associated gene) (Brychkova et al., 2007, ibid; Buchanan-Wollaston V. et al., 2005 Plant J 42, 567-585; Miao Y. et al., 2004, ibid) in Atxdh1 mutant leaves compared to wild type leaves (FIG. 3, upper panels). Marker genes that emphasize late processes in senescence are SRG1 (senescence related gene1, a member of Fe(II)/ascorbate oxidase gene family) and XERO1/TAS14 (dehydrin; Alsheikh M. K. et al., 2005 Plant Cell Environ 28, 1114-1122; Brychkova et al., 2007, ibid; Callard D. et al., 1996 Plant Physiol 112, 705-715; Weaver L. M. et al., 1998, ibid). After 6 days they were induced 390-fold in Col wild type plants and were yet 2-6-fold higher in the mutant lines (FIG. 3, middle panels). Similarly, the transcript level of the Cys protease senescence-associated gene 12 (SAG12), a common marker of leaf senescence (Gepstein et al., 2003 Plant J 36, 629-642), exhibited earlier and higher expression in Atxdh1 compromised plants (see FIG. 10).

The chlorophyll-degradation gene ACD1 (accelerated cell death1) is involved in senescence-associated chlorophyll breakdown (Tanaka et al., 2003, ibid) while SGN1 (stay-green protein1) is involved in chlorophyll catabolism during development (Park et al., 2007, ibid). The transcript levels of these genes were rapidly induced already after 1 day in darkness and were maintained at higher levels in Atxdh1 mutants in comparison to those of Col plants (FIG. 3, lower panels). These results indicate that the presence of AtXDH1 plays an important role in impeding symptoms and molecular events indicative of pre-mature senescence in response to dark-induced stress.

Example 5: XDH and Non-XDH Superoxide Generating Activities

Figure 4A:
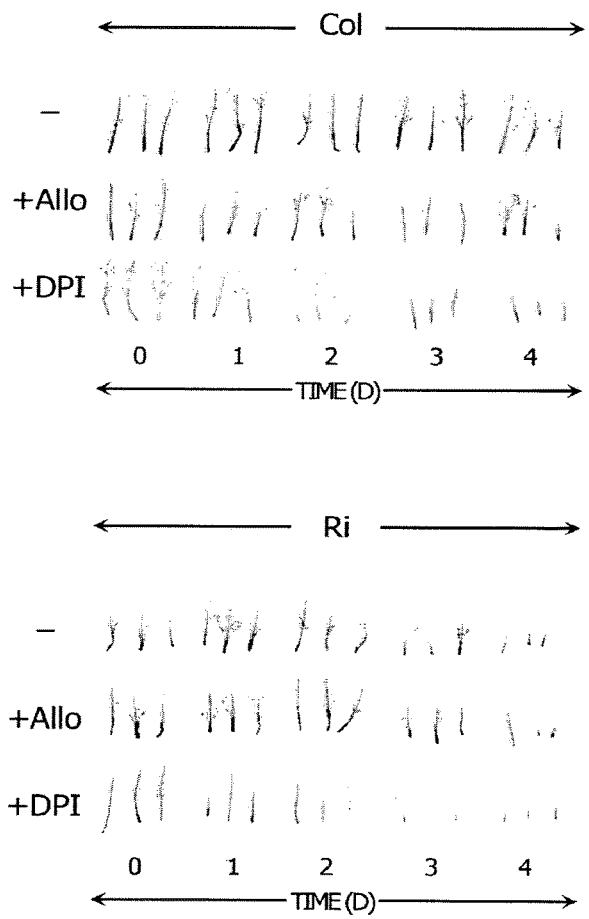
FIGS. 4a-4b show Nitroblue tetrazolium (NBT)-$O_2^-$ generation in wild type (Col) and xdh1 RNA interference (Ri) plants in response to dark treatment.
Figure 4B:
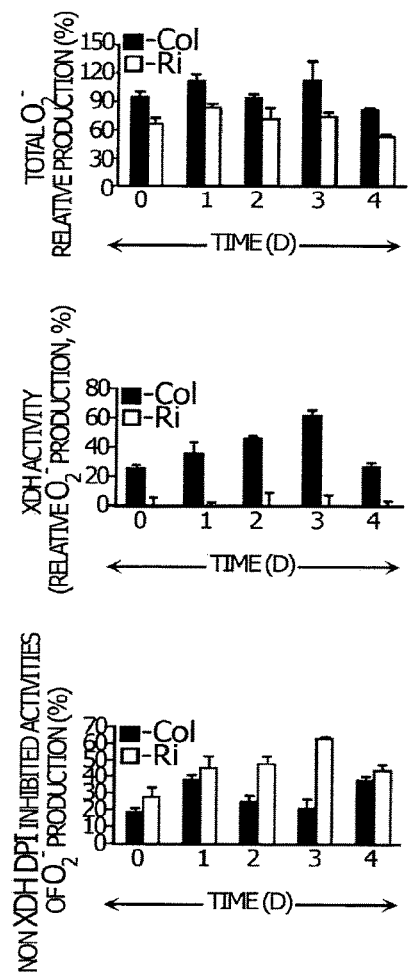

Reference is now made to FIG. 4 which shows quantitative analysis of NBT-$O_2^-$ production in leaves in response to dark treatment. Plant XDH reactions can use as electron receptors molecular oxygen yielding $O_2^-$, or if available, non-reduced $NAD^+$ (Hesberg C. et al., 2004 J Biol Chem 279, 13547-13554; Nguyen J. 1986 Physiologie Vegetale 24, 263-281; Yesbergenova et al., 2005, ibid). The resultant superoxide may further impinge on the physiology of dark-induced stress. In an attempt to illuminate the situation in vivo, reactive oxygen species (ROS) sources were estimated during dark treatment by the differential use of 2 inhibitors, allopurinol and diphenylene iodonium (DPI). The XDH inhibitor allopurinol is converted to alloxanthine, which remains tightly attached to the substrate-binding pocket in the MoCo domain, thereby preventing further substrate turnover (Harrison 2002, ibid; Hesberg et al., 2004, ibid). In contrast, DPI is a suicide inhibitor of flavin-containing enzymes and can be used to estimate both XDH and e.g. NADPH oxidase activities (Sagi and Fluhr, 2001, ibid; Yesbergenova et al., 2005, ibid). To this end, rosette leaves of dark-treated plants were examined by NBT infiltration for the detection of superoxides (Fryer et al., 2002, ibid). During dark treatment wild-type leaves had a basal level of total superoxide that remained within ±15% of the light control (not shown). In contrast, mutant leaves showed ~30% lower total levels of NBT reduction, indicating that XDH activity has a measurable contribution to the redox milieu of the plant as has been observed previously (Yesbergenova et al., 2005 ibid). The addition of the XDH inhibitor, allopurinol, gives an independent measure of XDH-dependent superoxide activity. As shown in FIG. 4b (middle panel) a nearly 3-fold increase in XDH-dependent superoxide production was obtained in the dark on day 3. In contrast, no such rise was detected in XDH mutant plants. An estimate of the residual XDH activity, due to either partial allopurinol inhibition or of $O_2^-$ production by a non-XDH source such as NADPH oxidase activity was obtained by simultaneous subtraction of +DPI from +allopurinol leaf scan values (FIG. 4b, lower panel). In this case $O_2^-$ production rose in the mutant plants during the dark (i.e. the DPI inhibited activities) more than in the wild type plants. Thus, in XDH compromised plants other sources of ROS can, in part, compensate in the dark for the loss of ROS supplied by XDH. Taken together, the XDH activity measured by superoxide production increased in vivo in the dark and makes a significant contribution to the leaf redox milieu.

Example 6: Dark Treatment Modifies Accumulation of Purine Metabolites

Reference is now made to FIG. 5 in which analysis of the purine metabolites, xanthine, allantoin and allantoate, in response to dark stress, is shown. It was examined whether the detected changes in XDH1 activity impinge on the accumulation of xanthine and/or ureides during the dark treatment and the subsequent recovery in the light. In wild type (Col) plants the xanthine level did not change during dark treatment over the low basal level (FIG. 5a). However, the basal level of xanthine content in Atxdh1 mutants was more than 10-fold higher than in Col plants although hypoxanthine levels remained below the detection limits. The xanthine level significantly increased in Atxdh1 mutant leaves upon dark treatment reaching over 10-fold the basal level in mutant plants and 100-fold the level detected in wild type plants. This level was only slightly reduced during the recovery period (FIG. 5a), indicating that potential XDH2 activity can play a typically minor role in the control of this xanthine pool. Thus, the presence of the XDH1 mutation unmasks a transient but significant increase in purine catabolic flux that occurs during the dark.

Figure 5B:
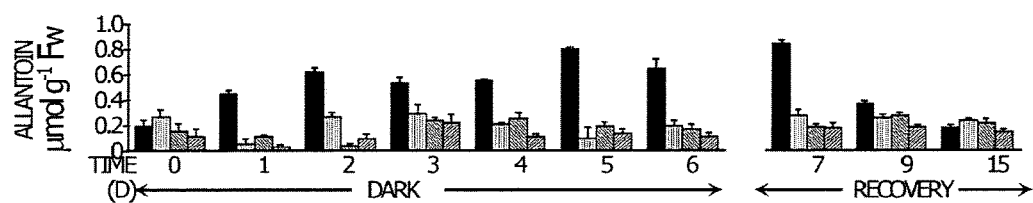
Figure 5C:
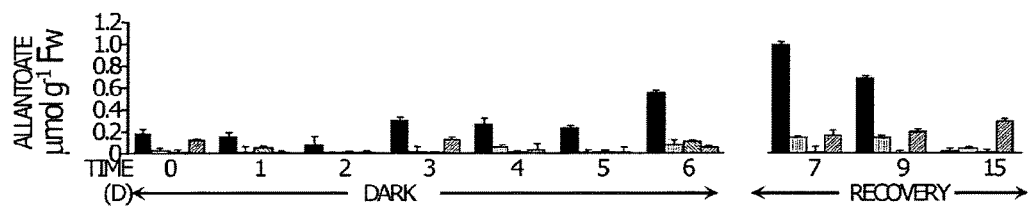

XDH activity produces urate which is rapidly converted to the ureides, allantoin and allantoate (Nguyen, 1986, ibid; Sagi et al., 1998 ibid). Unexpectedly, their levels were found to be significantly enhanced in wild type Col leaves upon exposing plants to dark treatment (5-fold; FIGS. 5b, 5c, dark). The accumulation may suggest that in wild type plants the downstream processing of ureides is transiently blocked. Interestingly, transfer of dark-treated wild type plants to the light after 6 days in the dark resulted in the gradual reduction of ureides that started after the first day and reached a basal level on the 9th day in the light (day 15, FIGS. 5b and 5c, recovery). In Atxdh1 mutant leaves, basal levels of allantoin and allantoate were detected and were similar to wild type levels. Their presence may represent XDH2 activity, residual XDH1 activity or represent an alternative pathway to ureide biosynthesis. Importantly, the level of allantoin and allantoate in Atxdh1 mutant leaves remained low during dark stress, or upon recovery (FIGS. 5b, 5c). The results indicate that AtXDH1 activity plays a pivotal role in dark-induced purine catabolism by facilitating the production of ureides.

Figure 6:
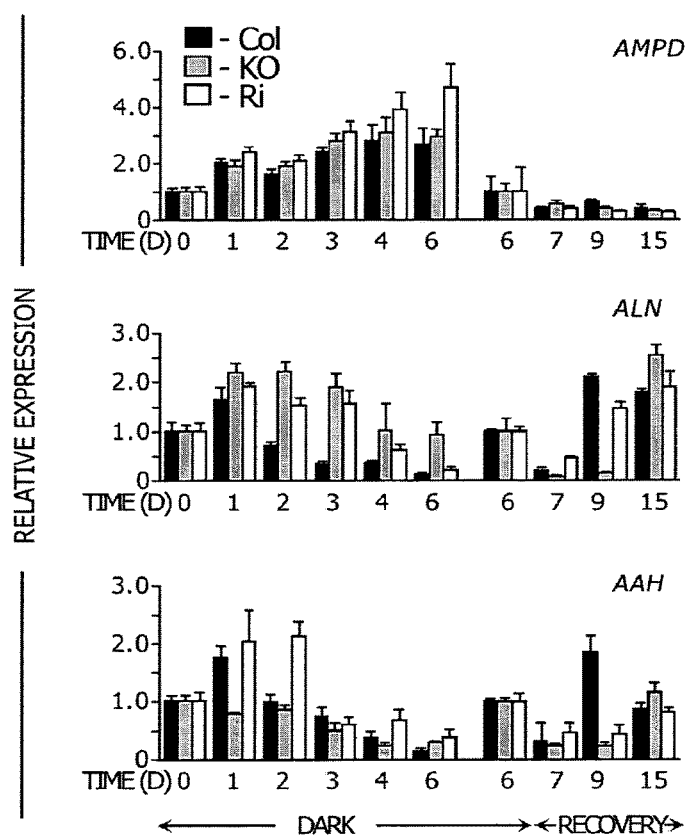
FIG. 6 demonstrates transcript expression levels of *Arabidopsis* purine catabolism genes, AMP deaminase (AMPD), allantoinase (ALN) and allantoate amidinohydrolase (AAH) during dark stress and subsequent recovery period. Quantitative analysis of transcripts by real-time RT-PCR was performed using wild-type (Col) and XDH compromised plants (KO, SALK 148364 Atxdh1 T-DNA insertion line; Ri, means of three xdh RNA interference lines) kept in the dark for 6 days and transferred to a 16 h light/8 h dark regime for recovery during additional 9 days. The expressions of each dark treated line was compared to the untreated line after normalization to the *Arabidopsis* EF-1α gene product (At5g60390) and is presented as the relative expression on day 0 or, for the recovery period, compared to the value of the dark treated line after 6 days in dark. Values are means±SEM (n=3).
Figure 12:
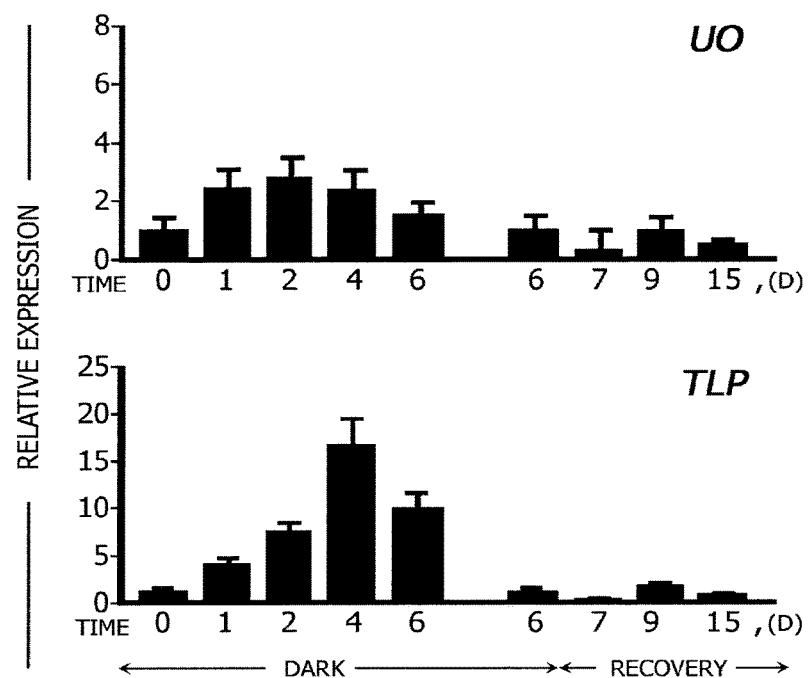
FIG. 12 shows transcript expression of *Arabidopsis* purine catabolism genes, encoding urate oxidase (UO) and transthyretin-like protein (TLP), is wild type (Col) plants exposed to dark stress of 6 days and subsequent recovery period of 16 h light/8 h dark regime for 9 days. Quantitative analysis of transcripts was performed by real-time RT-PCR compared to the untreated plant after normalization to the *Arabidopsis* EF-1α gene product (At5g60390). Data are presented as relative expression compared to day 0 or, for the recovery period, compared to the value of the dark treated plant after 6 days in the dark. Values are means±SEM (n=3).

Example 7: Dark-Induced Stress Modifies Transcript Levels of Genes Involved in Purine Catabolism Up-Stream and Down-Stream to XDH Reference is now made to FIG. 6 which shows quantitative analysis of transcripts by real-time RT-PCR performed using wild-type (Col) and XDH compromised plants (KO, SALK 148364 Atxdh1 T-DNA insertion line; Ri, means of three XDH RNA interference lines) after being kept in the dark for 6 days and transferred to a 16 h light/8 h dark regime for recovery during additional 9 days. The rise in ureide levels implies a bottleneck in their remobilization during the extended dark period, which should be reflected in an increase or decrease of transcripts in the catabolic pathway. AMPD, catalyzing the conversion of AMP to IMP, is the first committed step in purine catabolism (Zrenner R. et al., 2006 Annu Rev Plant Biol 57, 805-836). Upon transfer to dark, AMPD transcript expression level rapidly rises in both Col and Atxdh1 mutants and falls upon exposure to light (FIG. 6, upper panel). In addition, transcript expression of the peroxisomal enzymes UO and TLP, thought to be involved in ureides production (Reumann S. et al., 2007 Plant Cell, tpc.107.050989), followed similar pattern of transcript induction during dark stress and subsequent recovery period, as exhibited by AMPD and XDH1 (FIG. 12). In contrast, ALN that converts allantoin to allantoate and AAH that converts allantoate to ureidoglycolate were enhanced on day one of the dark treatment but then declined significantly to below the basal level on the 4th and 6th day. The latter reduction coincides with the timing of the increase in ureides accumulation. Upon re-exposure to light the transcripts again returned to near basal levels (FIG. 6, middle and lower panels). Thus, transcripts upstream and downstream from ureide biosynthesis were regulated reciprocally. The result is consistent with the observed rise in ureide levels and indicates that a transcriptional component exists in the control of allantoin and allantoate accumulation during dark treatment (FIG. 5).

Example 8: Purine Remobilization is Also Reflected in Leaf Age

Reference is made to FIG. 7, which shows the influence of ageing on leaf phenotype, purine metabolite level and transcript expression in wild type and Atxdh1 compromised plants.

Figure 7A:
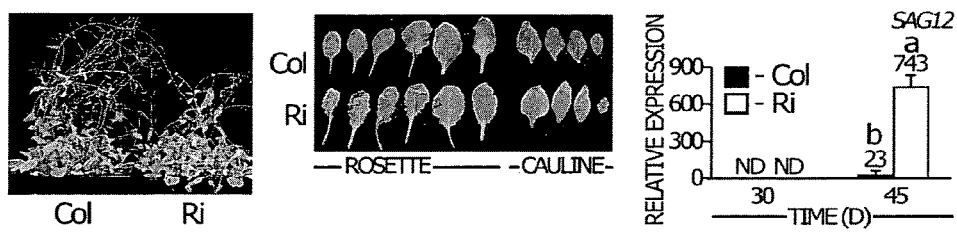
FIGS. 7a-7c demonstrate the influence of ageing on leaf phenotype, purine metabolite level and transcript expression in wild type and XDH1 compromised plants.
Figure 7B:
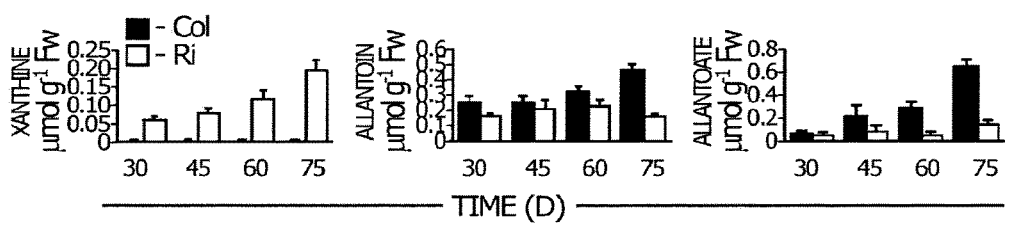
Figure 7C:
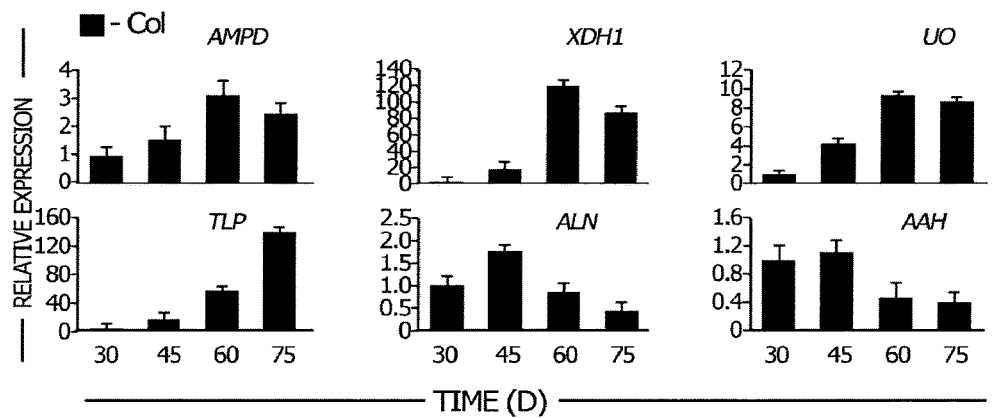

Dark treatment stimulates remobilization of metabolites which should in part mimic processes that occur during ageing. To examine this, transcripts related to ureides synthesis were examined in wild type and XDH1 mutant plants over the entire plant life. With increasing age, rosette leaves of XDH mutant plants yellowed earlier than wild-type Col plants and exhibited a significantly higher fold level of the SAG12 transcript (FIG. 7a). The transcripts level of enzymes leading to allantoin and allantoate production in wild type plants, AMPD, XDH1, UO and TLP were elevated with age. In contrast, a concomitant reduction was observed in the transcript level of allantoin and allantoate utilization enzymes, ALN and AAH (FIG. 7c). Consistent with these observations, the XDH mutant showed age-dependent accumulation of xanthine and wild type plants showed gradual accumulation of the ureides allantoin and allantoate (FIG. 7b). Interestingly, the levels of xanthine and ureides that accumulate with plant age were similar to the accumulation detected during acute dark stress (FIG. 5) and may indicate the catabolic capacity of purine metabolism.

Example 9: Role of Xanthine and Ureides in Cellular Protection During Dark-Induced Stress Reference is made to FIG. 8 which shows responses of *Arabidopsis* wild-type (Col) and xdh RNA interference (Ri) plants to application of the purine catabolites: xanthine, allantoin and allantoate. The dark-induced loss of chlorophyll and the accelerated cell death during recovery may be due to the accumulation of excess oxypurines (FIG. 5a) or to the lack of a protective environment provided by ureides (FIGS. 5b and 5c) or both. To examine this directly, leaf discs cut from Col and Atxdh mutants rosette leaves were treated with xanthine for 48 h in the dark and were sampled after 24 h in the light. Application of 1 mM xanthine (in the range of the calculated xanthine level that accumulates in dark-treated mutant plants) caused a reduction in chlorophyll which was exacerbated in the presence of allopurinol in both wild type and mutant Ri lines (FIG. 8a). Interestingly, Col leaf discs that exhibited the lowest chlorophyll degradation contained enhanced allantoin and allantoate levels (FIG. 8a). The observations indicate that ureides may protect chlorophyll from degradation during dark treatment and the recovery period. To elucidate the role of allantoin and allantoate directly, leaf discs were treated with 0.1 mM allantoin or allantoate. In this case, both types of ureides protected the treated leaf discs from chlorophyll degradation after 48 h dark treatment (FIG. 8b). Importantly, the protection by the ureides was afforded in spite of the significant accumulation of xanthine in allopurinol-treated Col plants and Atxdh mutants (FIG. 8b). These results suggest that chlorophyll degradation resulting from dark-induced stress and subsequent light period is due to the lack of accumulation of ureides that likely overcome a negative role of xanthine or other dark-induced components.

Reference is also made to FIG. 14 showing that allantoin application prevents leaf spoilage in Parsley. Parsley leaf discs were kept for 2 days in the light and then for 2 days in the dark with or without the addition of 0 to 10 mM allantoin. Undetached leaves kept in the light served as control (CL). The influence of allantoin application on senescence in parsley was examined by measuring the chlorophyll content relative to the content in the control undeteched leaves. In this particular case application of 0.1-0.5 mM allantoin was particularly effective in preventing the chlorophyll loss.

Reference is further made to FIG. 15, which shows the response of tomato to extended dark stress and recovery in light thereafter and the effect of application of exogenous allantoin on leaf chlorophyll content. Allantoin level in the $1^{st}$, $3^{rd}$ and $5^{th}$ leave of wild type tomato plants was measured during 12 days in the dark and during 10 days of recovery in the light thereafter. FIG. 15a show that exposing tomato plants to dark stress increases the allantoin level in the leaves. FIG. 15b shows that application of allantoin to tomato leaf discs kept in the dark for 2 days and then transferred to the light for additional two days delayed the chlorophyll degradation.

These results show that application of 0.1-10 mM allantoin protects leaves from chlorophyll degradation and yellowing. According to one embodiment 0.1 mM of allantoin, 0.5 mM of allantoin or any concentration of allantoin in this range are sufficient to prevent yellowing.

Example 10: A Role for Ureides as Cellular Scavengers

Reference is made to FIG. 9, which shows ROS accumulation in the presence of allantoin and allantoate in *Arabidopsis* wild-type (Col) and xdh1 RNA interference (Ri) lines. ROS accumulation has been shown to initiate chlorophyll degradation (Rentel M. C. et al., 2004 Nature 427, 858-861) and the enhanced chlorophyll degradation in leaves in the absence of XDH may result from ROS production during dark stress (FIG. 4; Guo and Crawford 2005 ibid). In light of the protective effect afforded by the ureides application, it is possible that they act as cellular protectants through ROS scavenging. To investigate the effect of ureides on chlorophyll integrity and cellular scavenging capability, leaf discs were treated with allantoin and allantoate and examined for chlorophyll, $H_2O_2$ and superoxide levels.

Figure 9A:
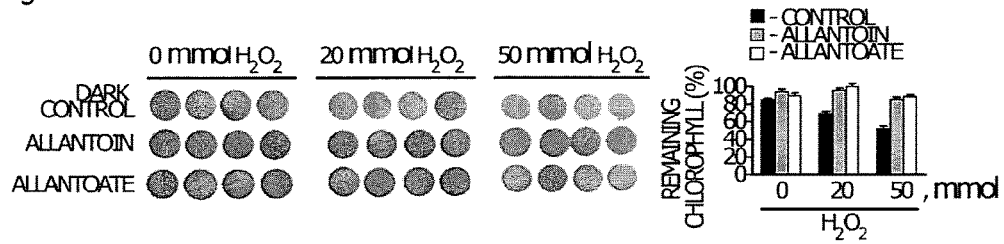
FIGS. 9a-9c show reactive oxygen species (ROS) accumulation in the presence of allantoin and allantoate in *Arabidopsis* wild-type (Col) and xdh1 RNA interference (Ri) lines.

Remaining chlorophyll was examined after the addition of 0.1 mM allantoin or allantoate for 24 h and subsequent application of 20 or 50 mM $H_2O_2$ for 6 h. The treated discs showed a significant increase in remaining chlorophyll (26 to 31% for 20 mM H2O2 and 32 to 36% for 50 $H_2O_2$ mM, respectively; FIG. 9*a*) indicating that ureides can protect leaves from ROS.

Figure 9B:
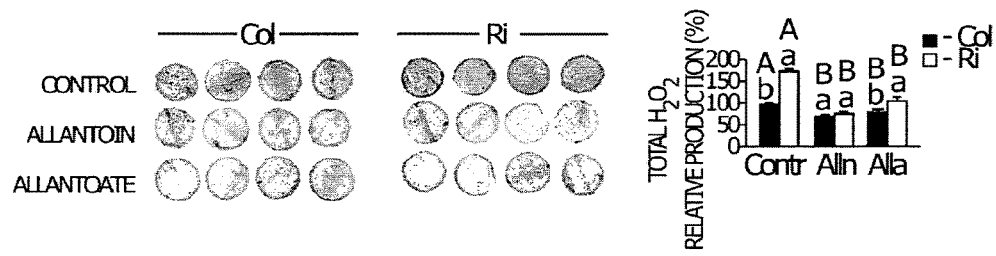
Figure 9C:
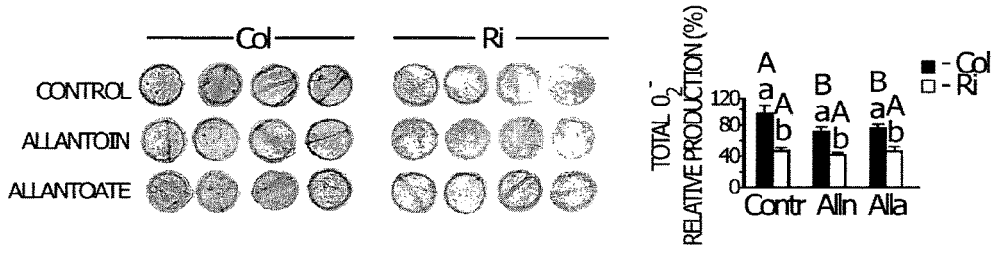

The concomitant accumulation of internal ROS as $H_2O_2$ was examined by application of 3,3'-diaminobenzidine (DAB). Mutant Ri lines showed 50% more DAB staining after 24 h dark treatment (FIG. 9*b*). When the discs were treated with allantoin or allantoate a significant 2-fold reduction in DAB staining intensity was observed. NBT staining for the presence of superoxide revealed reduced staining in Ri lines (FIG. 9*c*) that had been described previously for whole leaves (FIG. 4). The addition of allantoin/allantoate significantly reduced staining in the Col lines but not the Ri lines. The results indicate that the presence of ureides diminishes $H_2O_2$ accumulation and are correlated with the observation of reduced chlorophyll degradation.

---

What is claimed is:

1. A method of extending the post-harvest shelf life of a fresh mature plant produce, the method comprising:
   (a) harvesting the fresh mature produce, wherein the fresh mature produce is selected from the group consisting of: vegetable, fruit, cut branches, and flower; and
   (b) applying to the fresh mature produce ready for harvest, either before or after harvest, a composition comprising at least one ureide selected from the group consisting of: allantoin and allantoate, in an amount effective in extending the post-harvest shelf life of the harvested fresh mature produce and protecting the harvested fresh mature produce from post-harvest premature senescence, senescence, or both.

2. The method according to claim 1, wherein the composition comprises 0.001-10 mM of the at least one ureide.

3. The method according to claim 2, wherein the composition comprises 0.01-10 mM of the at least one ureide.

4. The method according to claim 2, wherein the composition comprises 0.1-0.5 mM of the at least one ureide.

5. The method of claim 1, wherein the applying step comprises spraying the fresh mature produce with the composition.

6. The method of claim 1, wherein the applying step comprises at least partially immersing the fresh mature produce in the composition.

7. A method of extending the post-harvest shelf life of a fresh plant produce, the method comprising:
   (a) harvesting the fresh produce, wherein the fresh produce is selected from the group consisting of: vegetable, fruit, cut branches, and flower; and
   (b) applying to the fresh produce, either at or after harvest, a composition comprising at least one ureide selected from the group consisting of: allantoin and allantoate, in an amount effective in extending the post-harvest shelf life of the harvested fresh produce and protecting the harvested fresh produce from post-harvest premature senescence, senescence, or both.

8. The method of claim 7, wherein the composition comprises 0.001-10 mM of the at least one ureide.

9. The method of claim 8, wherein the composition comprises 0.01-10 mM of the at least one ureide.

10. The method of claim 8, wherein the composition comprises 0.1-0.5 mM of the at least one ureide.

11. The method of claim 7, wherein the applying step comprises spraying the fresh produce with the composition.

12. The method of claim 7, wherein the applying step comprises at least partially immersing the fresh produce in the composition.

* * * * *